US012480151B2

(12) United States Patent
Distel

(10) Patent No.: US 12,480,151 B2
(45) Date of Patent: Nov. 25, 2025

(54) DNA PRESERVATION IN BIOLOGICAL SPECIMENS USING METAL CHELATORS

(71) Applicant: Northeastern University, Boston, MA (US)

(72) Inventor: Daniel Distel, Windham, NH (US)

(73) Assignee: Northeastern University, Boston, MA (US)

( * ) Notice: Subject to any disclaimer, the term of this patent is extended or adjusted under 35 U.S.C. 154(b) by 1114 days.

(21) Appl. No.: 17/180,159

(22) Filed: Feb. 19, 2021

(65) Prior Publication Data

US 2021/0267189 A1 Sep. 2, 2021

Related U.S. Application Data

(60) Provisional application No. 62/978,487, filed on Feb. 19, 2020.

(51) Int. Cl.

| | |
|---|---|
| ***C12N 15/10*** | (2006.01) |
| ***A01N 1/122*** | (2025.01) |
| ***A01N 1/128*** | (2025.01) |
| ***C12N 15/11*** | (2006.01) |
| ***C12Q 1/68*** | (2018.01) |
| ***C12Q 1/6806*** | (2018.01) |

(52) U.S. Cl.
CPC ........... *C12Q 1/6806* (2013.01); *A01N 1/122* (2025.01); *A01N 1/128* (2025.01)

(58) Field of Classification Search
None
See application file for complete search history.

(56) References Cited

U.S. PATENT DOCUMENTS 8,735,054 B1 * 5/2014 Sun .......................... A01N 1/00 435/1.1

FOREIGN PATENT DOCUMENTS

| | | | |
|---|---|---|---|
| CN | 110016475 | * | 7/2019 |
| WO | WO 2011100752 | * | 8/2011 |

OTHER PUBLICATIONS

ECA Academy, What are the regulatory Definitions for "Ambient", "Room Temperature" and "Cold Chain"?, 2017, downloaded Mar. 6, 2024 pp. 1-4.*
McNevin, D, Preservation of and DNA Extraction from Muscle Tissue, Chapter 4 from William Goodwin (ed.), Forensic DNA Typing Protocols, Methods in Molecular Biology, vol. 1420, 2016, pp. 43-53.*
Zhou et al translation of CN 110016475, 2019, pp. 1-10.*
Sharpe et al., "DESS deconstructed: Is EDTA solely responsible for protection of high molecular weight DNA in this common tissue preservative?," PLoS One 15(8): e0237356 (2020).
Sharpe et al., "Optimizing DNA Preservation for Conservation Efforts: What is the Active Ingredient in DMSO-salt?," presented at the 2019 Massachusetts Association of Conservation Commissions Annual Environmental Conference on Mar. 2, 2019.

* cited by examiner

*Primary Examiner* — Maria Marvich
(74) *Attorney, Agent, or Firm* — Foley Hoag LLP; Dana M. Gordon; Lawrence P. Tardibono

(57) ABSTRACT

Disclosed is a method for preserving high molecular weight DNA in biological tissue, comprising contacting for a period of time at a temperature the biological tissue with an aqueous solution comprising a compound having the structure:

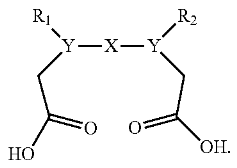

12 Claims, 19 Drawing Sheets

Specification includes a Sequence Listing.

1 day

| | Taxa | Time interval | Statistical test |
|---|---|---|---|
| %R | *Mytilus edulis* | 1 day | Friedman $\chi^2$ |
| | | 3 months | Friedman $\chi^2$ |
| | | 6 months | Friedman $\chi^2$ |
| | *Faxonius virilis* | 1 day | Repeated measures ANOVA |
| | | 3 months | Friedman $\chi^2$ |
| | | 6 months | Friedman $\chi^2$ |
| | *Alitta virens* | 1 day | Friedman $\chi^2$ |
| | | 3 months | Friedman $\chi^2$ |
| | | 6 months | Friedman $\chi^2$ |
| nY | *Mytilus edulis* | 1 day | Friedman $\chi^2$ |
| | | 3 months | Friedman $\chi^2$ |
| | | 6 months | Friedman $\chi^2$ |
| | *Faxonius virilis* | 1 day | Friedman $\chi^2$ |
| | | 3 months | Friedman $\chi^2$ |
| | | 6 months | Friedman $\chi^2$ |
| | *Alitta virens* | 1 day | Friedman $\chi^2$ |
| | | 3 months | Friedman $\chi^2$ |
| | | 6 months | Friedman $\chi^2$ |

| | Taxa | Test statistic | df | *p* value |
|---|---|---|---|---|
| %R | *Mytilus edulis* | $\chi^2 = 45.333$ | 8 | < 0.001* |
| | | $\chi^2 = 50.362$ | 8 | < 0.001* |
| | | $\chi^2 = 44.648$ | 8 | < 0.001* |
| | *Faxonius virilis* | $F = 2.952$ | 8 | 0.008* |
| | | $\chi^2 = 45.105$ | 8 | < 0.001* |
| | | $\chi^2 = 43.124$ | 8 | < 0.001* |
| | *Alitta virens* | $\chi^2 = 66.080$ | 8 | < 0.001* |
| | | $\chi^2 = 65.387$ | 8 | < 0.001* |
| | | $\chi^2 = 38.067$ | 8 | < 0.001* |
| nY | *Mytilus edulis* | $\chi^2 = 24.571$ | 8 | 0.002* |
| | | $\chi^2 = 45.676$ | 8 | < 0.001* |
| | | $\chi^2 = 42.400$ | 8 | < 0.001* |
| | *Faxonius virilis* | $\chi^2 = 11.771$ | 8 | 0.162 |
| | | $\chi^2 = 42.171$ | 8 | < 0.001* |
| | | $\chi^2 = 43.390$ | 8 | < 0.001* |
| | *Alitta virens* | $\chi^2 = 62.400$ | 8 | < 0.001* |
| | | $\chi^2 = 66.693$ | 8 | < 0.001* |
| | | $\chi^2 = 48.100$ | 8 | < 0.001* |

FIG. 4

| | | 1 day | | | | | | | | | | | |
|---|---|---|---|---|---|---|---|---|---|---|---|---|---|
| | | Yield (µg DNA) | | | Total Normalized Yield (µg DNA/mg tissue) | | | nY (µg DNA/mg tissue) | | | %R | | |
| | | mean | sd | N | mean | sd | N | mean | sd | N | mean | sd | N |
| *Mytilus edulis* | DESS | 8.7029 | 5.9717 | 7 | 0.7747 | 0.4834 | 7 | 0.3674 | 0.2289 | 7 | 47.08 | 3.14 | 7 |
| | DE | 7.6243 | 3.9459 | 7 | 0.7397 | 0.4333 | 7 | 0.2837 | 0.1598 | 7 | 39.14 | 4.27 | 7 |
| | DSS | 17.0714 | 5.8846 | 7 | 1.7745 | 1.0795 | 7 | 0.1395 | 0.1309 | 7 | 11.85 | 15.62 | 7 |
| | ESS | 6.4786 | 5.6672 | 7 | 0.5451 | 0.5307 | 7 | 0.2450 | 0.2389 | 7 | 45.30 | 1.93 | 7 |
| | D | 14.6357 | 10.0298 | 7 | 0.6912 | 0.4172 | 7 | 0.0469 | 0.0997 | 7 | 4.51 | 6.05 | 7 |
| | E | 5.9543 | 2.0091 | 7 | 0.4219 | 0.1746 | 7 | 0.1636 | 0.0605 | 7 | 39.39 | 4.19 | 7 |
| | SS | 19.8129 | 7.2080 | 7 | 1.3500 | 0.4960 | 7 | 0.3071 | 0.1570 | 7 | 23.86 | 9.22 | 7 |
| | EtOH | 40.9571 | 15.8462 | 7 | 1.0017 | 0.2159 | 7 | 0.2353 | 0.0782 | 7 | 23.36 | 5.84 | 7 |
| | Fresh | 31.3571 | 20.0233 | 7 | 1.0947 | 0.5910 | 7 | 0.3066 | 0.1221 | 7 | 30.22 | 6.78 | 7 |
| *Foxonius viridis* | DESS | 0.7917 | 0.2778 | 7 | 0.0295 | 0.0146 | 7 | 0.0077 | 0.0034 | 7 | 26.51 | 3.91 | 7 |
| | DE | 0.9696 | 0.2016 | 7 | 0.0349 | 0.0113 | 7 | 0.0143 | 0.0051 | 7 | 40.55 | 4.26 | 7 |
| | DSS | 8.7193 | 13.3091 | 7 | 0.3199 | 0.5064 | 7 | 0.0791 | 0.0949 | 7 | 25.51 | 18.96 | 7 |
| | ESS | 0.8839 | 0.7247 | 7 | 0.0374 | 0.0419 | 7 | 0.0131 | 0.0192 | 7 | 28.74 | 8.62 | 7 |
| | D | 3.4197 | 2.9664 | 7 | 0.1465 | 0.1243 | 7 | 0.0238 | 0.0172 | 7 | 17.57 | 7.09 | 7 |
| | E | 0.7049 | 0.2364 | 7 | 0.0259 | 0.0099 | 7 | 0.0101 | 0.0059 | 7 | 36.96 | 11.52 | 7 |
| | SS | 3.1371 | 1.2346 | 7 | 0.1168 | 0.0609 | 7 | 0.0440 | 0.0424 | 7 | 33.11 | 23.24 | 7 |
| | EtOH | 2.2591 | 1.4130 | 7 | 0.0464 | 0.0301 | 7 | 0.0167 | 0.0119 | 7 | 36.56 | 8.08 | 7 |
| | Fresh | 1.1077 | 0.9347 | 7 | 0.0386 | 0.0344 | 7 | 0.0155 | 0.0136 | 7 | 39.86 | 8.31 | 7 |
| *Alitta virens* | DESS | 1.8872 | 1.2492 | 10 | 0.1783 | 0.3829 | 10 | 0.0931 | 0.2201 | 10 | 41.30 | 7.65 | 10 |
| | DE | 2.0241 | 0.9468 | 10 | 0.0812 | 0.0441 | 10 | 0.0344 | 0.0247 | 10 | 36.78 | 14.22 | 10 |
| | DSS | 1.5104 | 0.8050 | 10 | 0.0801 | 0.0846 | 10 | 0.0059 | 0.0062 | 10 | 7.39 | 1.17 | 10 |
| | ESS | 2.8420 | 1.2807 | 10 | 0.0985 | 0.0549 | 10 | 0.0528 | 0.0358 | 10 | 51.57 | 5.78 | 10 |
| | D | 1.0851 | 0.5876 | 10 | 0.0526 | 0.0327 | 10 | 0.0020 | 0.0016 | 10 | 3.69 | 2.25 | 10 |
| | E | 5.9840 | 1.9118 | 10 | 0.2438 | 0.0879 | 10 | 0.1161 | 0.0493 | 10 | 47.58 | 4.97 | 10 |
| | SS | 1.8500 | 0.5539 | 10 | 0.0593 | 0.0210 | 10 | 0.0141 | 0.0083 | 10 | 22.17 | 6.76 | 10 |
| | EtOH | 6.2790 | 2.1015 | 10 | 0.1430 | 0.0482 | 10 | 0.0422 | 0.0169 | 10 | 29.15 | 3.18 | 10 |
| | Fresh | 10.9010 | 5.0185 | 10 | 0.3677 | 0.2084 | 10 | 0.1469 | 0.0776 | 10 | 41.72 | 11.98 | 10 |

FIG. 8

| | | 3 months | | | | | | | | | | | |
|---|---|---|---|---|---|---|---|---|---|---|---|---|---|
| | | Yield (µg DNA) | | | Total Normalized Yield (µg DNA/mg tissue) | | | nY (µg DNA/mg tissue) | | | %R | | |
| | | mean | sd | *N* | mean | sd | *N* | mean | sd | *N* | mean | sd | *N* |
| *Mytilus edulis* | DESS | 17.3643 | 6.9406 | 7 | 1.1155 | 0.4690 | 7 | 0.5783 | 0.2098 | 7 | 53.50 | 5.94 | 7 |
| | DE | 25.9529 | 12.5080 | 7 | 1.2375 | 0.5615 | 7 | 0.5583 | 0.3196 | 7 | 40.20 | 14.61 | 7 |
| | DSS | 0.5756 | 0.0910 | 7 | 0.0376 | 0.0089 | 7 | 0.0012 | 0.0005 | 7 | 3.17 | 1.58 | 7 |
| | ESS | 14.0114 | 9.7129 | 7 | 0.8687 | 0.5909 | 7 | 0.4410 | 0.1927 | 7 | 55.57 | 10.03 | 7 |
| | D | 1.8229 | 0.5308 | 7 | 0.0884 | 0.0364 | 7 | 0.0011 | 0.0003 | 7 | 1.37 | 0.37 | 7 |
| | E | 18.8857 | 13.6520 | 7 | 0.8045 | 0.5217 | 7 | 0.3645 | 0.1459 | 7 | 50.44 | 9.76 | 7 |
| | SS | 0.6494 | 0.3423 | 7 | 0.1368 | 0.2835 | 7 | 0.0010 | 0.0022 | 7 | 0.75 | 0.53 | 7 |
| | EtOH | 49.3000 | 8.4751 | 7 | 1.2011 | 0.3020 | 7 | 0.1992 | 0.1516 | 7 | 15.37 | 9.07 | 7 |
| | Fresh | 24.2714 | 7.1435 | 7 | 0.7752 | 0.1679 | 7 | 0.2658 | 0.0932 | 7 | 33.79 | 7.37 | 7 |
| *Foxonius viridis* | DESS | 0.8530 | 0.3611 | 7 | 0.0355 | 0.0179 | 7 | 0.0082 | 0.0063 | 7 | 22.57 | 13.61 | 7 |
| | DE | 1.6390 | 1.6285 | 7 | 0.0683 | 0.0721 | 7 | 0.0288 | 0.0404 | 7 | 33.84 | 14.93 | 7 |
| | DSS | 0.4186 | 0.2732 | 7 | 0.0158 | 0.0127 | 7 | 0.0006 | 0.0006 | 7 | 3.85 | 2.12 | 7 |
| | ESS | 1.2183 | 0.9004 | 7 | 0.0558 | 0.0471 | 7 | 0.0238 | 0.0320 | 7 | 33.61 | 20.47 | 7 |
| | D | 0.4771 | 0.2798 | 7 | 0.0194 | 0.0095 | 7 | 0.0003 | 0.0002 | 7 | 1.66 | 0.62 | 7 |
| | E | 1.4491 | 1.2580 | 7 | 0.0584 | 0.0422 | 7 | 0.0307 | 0.0219 | 7 | 51.74 | 4.84 | 7 |
| | SS | 0.6617 | 0.5780 | 7 | 0.0208 | 0.0178 | 7 | 0.0005 | 0.0005 | 7 | 2.98 | 1.33 | 7 |
| | EtOH | 3.4943 | 1.3170 | 7 | 0.0699 | 0.0472 | 7 | 0.0288 | 0.0250 | 7 | 38.70 | 10.23 | 7 |
| | Fresh | 2.0300 | 1.1284 | 7 | 0.0674 | 0.0392 | 7 | 0.0228 | 0.0160 | 7 | 35.34 | 11.55 | 7 |
| *Alitta virens* | DESS | 4.1970 | 1.9863 | 10 | 0.1524 | 0.0663 | 10 | 0.0309 | 0.0444 | 10 | 17.37 | 20.18 | 10 |
| | DE | 0.7325 | 0.7644 | 10 | 0.0284 | 0.0288 | 10 | 0.0003 | 0.0002 | 10 | 1.75 | 1.08 | 10 |
| | DSS | 0.1292 | 0.0162 | 10 | 0.0051 | 0.0007 | 10 | 0.0001 | 0.0000 | 10 | 2.63 | 0.58 | 10 |
| | ESS | 3.4080 | 1.3968 | 10 | 0.1180 | 0.0408 | 10 | 0.0115 | 0.0073 | 10 | 10.06 | 6.64 | 10 |
| | D | 0.1512 | 0.0339 | 10 | 0.0065 | 0.0019 | 10 | 0.0002 | 0.0001 | 10 | 2.51 | 0.81 | 10 |
| | E | 1.2427 | 1.5308 | 10 | 0.0479 | 0.0631 | 10 | 0.0002 | 0.0002 | 10 | 1.22 | 0.93 | 10 |
| | SS | 0.1403 | 0.0321 | 10 | 0.0049 | 0.0012 | 10 | 0.0003 | 0.0001 | 10 | 5.19 | 1.46 | 10 |
| | EtOH | 6.3750 | 2.5859 | 10 | 0.1203 | 0.0601 | 10 | 0.0196 | 0.0131 | 10 | 17.23 | 10.34 | 10 |
| | Fresh | 5.8660 | 3.2954 | 10 | 0.1833 | 0.1092 | 10 | 0.0695 | 0.0289 | 10 | 40.46 | 8.94 | 10 |

FIG. 8 (cont'd)

| | | 6 months | | | | | | | | | | | |
|---|---|---|---|---|---|---|---|---|---|---|---|---|---|
| | | Yield (µg DNA) | | | Total Normalized Yield (µg DNA/mg tissue) | | | nY (µg DNA/mg tissue) | | | %R | | |
| | | mean | sd | *N* | mean | sd | *N* | mean | sd | *N* | mean | sd | *N* |
| *Mytilus edulis* | DESS | 23.3286 | 10.0011 | 7 | 1.6897 | 0.7693 | 7 | 0.6837 | 0.2320 | 7 | 43.55 | 8.85 | 7 |
| | DE | 24.8857 | 9.3142 | 7 | 1.1461 | 0.4908 | 7 | 0.5573 | 0.2518 | 7 | 48.50 | 11.14 | 7 |
| | DSS | 0.6177 | 0.4738 | 7 | 0.0349 | 0.0301 | 7 | 0.0012 | 0.0010 | 7 | 3.67 | 1.24 | 7 |
| | ESS | 27.4329 | 15.9590 | 7 | 1.8358 | 0.8126 | 7 | 0.6772 | 0.2140 | 7 | 40.45 | 12.99 | 7 |
| | D | 1.3554 | 1.3033 | 7 | 0.0629 | 0.0681 | 7 | 0.0044 | 0.0078 | 7 | 4.29 | 3.22 | 7 |
| | E | 33.7500 | 19.5948 | 7 | 1.4969 | 0.8675 | 7 | 0.5249 | 0.2132 | 7 | 40.97 | 16.38 | 7 |
| | SS | 0.2004 | 0.0503 | 7 | 0.0087 | 0.0017 | 7 | 0.0003 | 0.0001 | 7 | 3.18 | 0.71 | 7 |
| | EtOH | 37.7257 | 22.1245 | 7 | 1.4130 | 0.9664 | 7 | 0.3311 | 0.3996 | 7 | 18.13 | 13.59 | 7 |
| | Fresh | 152.8000 | 134.0373 | 7 | 4.8744 | 4.0518 | 7 | 1.0128 | 0.5618 | 7 | 25.95 | 8.45 | 7 |
| *Faxonius virilis* | DESS | 3.9914 | 2.3694 | 7 | 0.1560 | 0.0963 | 7 | 0.0811 | 0.0545 | 7 | 50.84 | 2.63 | 7 |
| | DE | 6.6186 | 3.4301 | 7 | 0.2029 | 0.0795 | 7 | 0.1027 | 0.0590 | 7 | 47.35 | 15.62 | 7 |
| | DSS | 0.5303 | 0.6055 | 7 | 0.0112 | 0.0056 | 7 | 0.0005 | 0.0003 | 7 | 4.33 | 1.71 | 7 |
| | ESS | 3.8821 | 2.1493 | 7 | 0.1261 | 0.0753 | 7 | 0.0553 | 0.0283 | 7 | 43.73 | 11.35 | 7 |
| | D | 0.2516 | 0.0483 | 7 | 0.0082 | 0.0029 | 7 | 0.0002 | 0.0001 | 7 | 3.13 | 1.94 | 7 |
| | E | 11.1457 | 4.5552 | 7 | 0.3387 | 0.1980 | 7 | 0.1937 | 0.1203 | 7 | 54.35 | 9.91 | 7 |
| | SS | 0.1971 | 0.0457 | 7 | 0.0055 | 0.0023 | 7 | 0.0002 | 0.0001 | 7 | 4.24 | 0.81 | 7 |
| | EtOH | 22.0614 | 15.8466 | 7 | 0.6723 | 0.5016 | 7 | 0.2811 | 0.1994 | 7 | 44.27 | 5.64 | 7 |
| | Fresh | 8.4477 | 8.7750 | 7 | 0.2736 | 0.2819 | 7 | 0.1170 | 0.1283 | 7 | 38.93 | 13.61 | 7 |
| *Alitta virens* | DESS | 2.0437 | 2.1947 | 9 | 0.0888 | 0.1001 | 9 | 0.0177 | 0.0332 | 9 | 13.00 | 12.82 | 9 |
| | DE | 0.3194 | 0.1844 | 9 | 0.0134 | 0.0100 | 9 | 0.0006 | 0.0005 | 9 | 5.14 | 3.89 | 9 |
| | DSS | 0.1386 | 0.0231 | 10 | 0.0062 | 0.0016 | 10 | 0.0002 | 0.0001 | 10 | 3.05 | 0.91 | 10 |
| | ESS | 1.0487 | 1.0845 | 10 | 0.0410 | 0.0454 | 10 | 0.0093 | 0.0135 | 10 | 17.81 | 11.24 | 10 |
| | D | 0.1529 | 0.0419 | 10 | 0.0075 | 0.0027 | 10 | 0.0005 | 0.0004 | 10 | 5.71 | 3.72 | 10 |
| | E | 0.5075 | 0.7740 | 10 | 0.0254 | 0.0435 | 10 | 0.0041 | 0.0117 | 10 | 5.19 | 7.33 | 10 |
| | SS | 0.1536 | 0.0338 | 10 | 0.0055 | 0.0019 | 10 | 0.0003 | 0.0003 | 10 | 3.97 | 3.33 | 10 |
| | EtOH | 17.2220 | 12.5778 | 10 | 0.5039 | 0.3534 | 10 | 0.0719 | 0.0819 | 10 | 11.89 | 7.00 | 10 |
| | Fresh | 18.7400 | 4.4677 | 10 | 0.5875 | 0.1415 | 10 | 0.2401 | 0.0710 | 10 | 41.37 | 8.64 | 10 |

FIG. 8 (cont'd)

| | | DESS | | DE | | DSS | | ESS | |
|---|---|---|---|---|---|---|---|---|---|
| | | *avg* | *SD* | *avg* | *SD* | *avg* | *SD* | *avg* | *SD* |
| *Mytilus Edulis* | *1 d* | 47.1 | 3.1 | 39.1 | 4.3 | 11.9 | 15.6 | 45.3 | 1.9 |
| | *3 m* | 53.5 | 5.9 | 40.2 | 14.6 | 3.2 | 1.6 | 55.6 | 10.0 |
| | *6 m* | 43.6 | 8.9 | 48.5 | 11.1 | - | - | 40.4 | 13.0 |
| *Faxonius virilis* | *1 d* | 26.5 | 3.9 | 40.6 | 4.3 | 25.5 | 19.0 | 28.7 | 8.6 |
| | *3 m* | 22.6 | 13.6 | 33.8 | 14.9 | 3.9 | 2.1 | 33.6 | 20.5 |
| | *6 m* | 50.8 | 2.6 | 47.3 | 15.6 | - | - | 43.7 | 11.4 |
| *Alitta Virens* | *1 d* | 41.3 | 7.7 | 36.8 | 14.2 | 7.4 | 1.2 | 51.6 | 5.8 |
| | *3 m* | 17.4 | 20.2 | 1.8 | 1.1 | - | - | 10.1 | 6.6 |
| | *6 m* | 13.0 | 12.8 | - | - | - | - | 19.6 | 10.3 |

| | | D | | E | | SS | | EtOH | | Fresh | |
|---|---|---|---|---|---|---|---|---|---|---|---|
| | | *avg* | *SD* | *avg* | *SD* | *avg* | *SD* | *avg* | *SD* | *avg* | *SD* |
| *Mytilus Edulis* | *1 d* | 4.5 | 6.1 | 39.4 | 4.2 | 23.9 | 9.2 | 23.4 | 5.8 | 30.2 | 6.8 |
| | *3 m* | - | - | 50.4 | 9.8 | 0.8 | 0.5 | 15.4 | 9.1 | 33.8 | 7.4 |
| | *6 m* | - | - | 41.0 | 16.4 | - | - | 18.1 | 13.6 | 25.9 | 8.5 |
| *Faxonius virilis* | *1 d* | 17.6 | 7.1 | 37.0 | 11.5 | 33.1 | 23.2 | 36.6 | 8.1 | 39.9 | 8.3 |
| | *3 m* | 1.7 | 0.6 | 51.7 | 4.8 | 3.0 | 1.3 | 38.7 | 10.2 | 35.3 | 11.5 |
| | *6 m* | - | - | 54.3 | 9.9 | - | - | 44.3 | 5.6 | 38.9 | 13.6 |
| *Alitta Virens* | *1 d* | 3.7 | 2.2 | 47.6 | 5.0 | 22.2 | 6.8 | 29.2 | 3.2 | 41.8 | 12.0 |
| | *3 m* | - | - | 1.2 | 0.9 | 3.2 | 1.5 | 17.2 | 10.3 | 40.5 | 8.9 |
| | *6 m* | - | - | - | - | - | - | 12.6 | 7.0 | 42.4 | 8.5 |

FIG. 9

SEQUENCE LISTING

```
<160> NUMBER OF SEQ ID NOS: 2

<210> SEQ ID NO 1
<211> LENGTH: 43
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 1
tgtaaaacga cggccagtgg tcaacaaatc ataaagatat tgg 43

<210> SEQ ID NO 2
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
caggaaacag ctatgactaa acttcagggt gaccaaaaaa tca 43

DNA PRESERVATION IN BIOLOGICAL SPECIMENS USING METAL CHELATORS

RELATED APPLICATION

This application claims the benefit of priority to U.S. Provisional Patent Application No. 62/978,487, filed Feb. 19, 2020.

SEQUENCE LISTING

The instant application contains a Sequence Listing which has been submitted electronically in ASCII format and is hereby incorporated by reference in its entirety. Said ASCII copy, created on May 10, 2021, is named NEX-07901_SL.txt and is 746 bytes in size.

BACKGROUND

The growing importance of DNA-based research has created increasing demand for methods that can preserve high-quality DNA in biological samples. A number of available preservation techniques can delay the degradation of DNA in tissue samples (Nagy, Z. T. 2010) but many are not easily adapted to the wide range of conditions commonly encountered by researchers working in the field. For example, cryopreservation is considered to be among the best techniques for preserving DNA in tissue (Camacho-Sanchez, M. et al. 2013; Dessauer, H. C. et al. 1996; Dawson, M. N. et al. 1998; Rocha, J. et al. 2014), but mechanical freezers and freezing agents such as dry ice and liquid nitrogen are expensive, bulky, hazardous and often subject to transportation and shipping restrictions. Similarly, ethanol (EtOH) is one of the most commonly used preservatives (Nagy, Z. T. 2010; Vink, C. J. et al. 2005; Gaither, M. et al. 2011), but is flammable, toxic, considered a controlled substance in many jurisdictions and may work best at cold temperatures (Santini, A. et al. 2007; Gray, M. A. et al. 2013). EtOH is also frequently subject to legal and travel restrictions (Proebstel, S. 1993; Kilpatrick, C. W. et al. 2002). While a variety of commercial products are available for DNA preservation, these formulations are typically proprietary, expensive, not amenable to user modification and incompletely documented in peer-reviewed literature. Hence, practical and well-documented solutions for field preservation of DNA in tissues are in high demand.

Seutin introduced a liquid preservative solution that has become widely known as DMSO-salt or DESS (Seutin, G. et al. 1991). The acronym DESS reflects the composition of this formulation, an aqueous solution containing 20% dimethyl sulfoxide (DMSO), 0.25 M ethylenediaminetetraacetic acid (EDTA) and saturated sodium chloride (NaCl), adjusted to pH 8.0. Although supporting data were not provided, the authors proposed that EDTA and NaCl may contribute to DNA preservation in tissue by chelating divalent cations required for the activity of nucleases and by denaturing nuclease enzymes, respectively, while DMSO may serve as a penetrant, helping to facilitate transport of these ingredients into cells (Seutin, G. et al. 1991).

Several qualities make DESS a desirable preservative for field applications. At the concentrations used, the components of DESS have low toxicity and present low risks of fire and explosion. Additionally, DESS is simple and inexpensive to prepare and can be stored and used at room temperature. Tissues stored in DESS have been reported to yield DNA of a similar quality and quantity as tissues preserved cryogenically or in other chemical preservatives (Dawson, M. N. et al. 1998; Gaither, M. et al. 2011; Seutin, G. et al. 1991). Researchers have routinely conducted a variety of common analyses including spectrophotometric analysis (Corthals, A. 2015), Southern blots (Seutin, G. et al. 1991), PCR amplifications (Dawson, M. N. et al. 1998; Gaither, M. et al. 2011; Gray, M. A. et al. 2013; Proebstel, S. 1993; Corthals, A. et al. 2015; Robertson, K. M. et al. 2013; Yoder, M. et al. 2006; Michaud, C. L. et al. 2011; Beknazarova, M. et al. 2017), fragment analysis (Gray, M. A. et al. 2013; Beknazarova, M. et al. 2017), qPCR (Gaither, M. et al. 2011; Corthals, A. 2015; Allen-Hall, A. et al. 2012), Sanger sequencing (Yoder, M. et al. 2006), and Illumina sequencing (Hernandez-Agreda, A. et al. 2018) using DNA extracted from tissues stored in DESS. Furthermore, DESS has been tested on a variety of organisms including jellyfish, anemones, snails and worms (Dawson, M. N. et al. 1998), nematodes (Yoder, M. et al. 2006; Beknazarova, M. et al. 2017), corals (Gaither, M. et al. 2011, coral microbial communities (Gray, M. A. et al. 2013; Hernandez-Agreda, A. et al. 2018), fish (Proebstel, S. 1993), cetaceans (Robertson, K. M. et al. 2013), bats (Corthals, A. et al. 2015), birds (Seutin, G. et al. 1991), mice (Kilpatrick, C. W. 2002), humans (Allen-Hall, A. et al. 2012), pigs (Michaud, C. L. et al. 2011), and fecal samples from baboons (Frantzen, M. et al. 1998); in most cases comparing favorably to other tested preservation methods over time intervals ranging from less than 1 day to more than 15 years. In our review of publications assessing the effectiveness of DESS, the median preservation period was 6 months, indicating that DESS can preserve DNA over time intervals suitable for many research applications (Dawson, M. N. et al. 1998; Gaither, M. et al. 2011; Gray, M. A. et al. 2013, Proebstel, S. 1993; Kilpatrick, C. W. 2002; Seutin, G. et al. 1991; Robertson, K. M. et al. 2013; Yoder, M. et al. 2006; Michaud, C. L. et al. 2011; Beknazarova, M. et al. 2017; Allen-Hall, A. et al. 2012; Frantzen, M. et al. 1998). As a result, the original recipe of Seutin has come into wide use, largely without modification.

Despite the success of DESS in many field applications, there are some concerns associated with its use. Although DMSO has low toxicity ($LD_{50}$ in rat=14,500 mg/kg, oral; 40,000 mg/kg, skin), it readily penetrates skin and may enhance the absorption of many potentially harmful chemicals into the bloodstream through skin contact. Thus, DMSO may become a serious health hazard if inadvertently combined with toxic materials (Brayton, C. F. 1986). Concentrated DMSO is also flammable and an irritant, which provides risk in preparation of DESS (Nagy, Z. T. 2010). EDTA and NaCl also have low toxicity (oral $LD_{50}$ in rat=2,000 mg/kg and 3,000 mg/kg, respectively). Both are used widely as additives in food, drugs and cosmetics, are nonflammable, chemically stable and are not known carcinogens. Nonetheless, gloves and eye protection are recommended when using DESS and its components. Because it is a saturated NaCl solution, DESS may be prone to precipitation, which may hamper the recovery of small or delicate samples. Finally, DMSO freezes at just below room temperature (19° C.) potentially limiting the usefulness of DESS at cold temperatures.

Although DESS is often referred to in literature as a DMSO-based preservative, e.g. DMSO salt-saturated solution (Hebert, P. D. et al. 2003), salt-saturated DMSO (Gaither, M. et al. 2011; Corthals, A. et al. 2015), DMSO-salt (Dawson, M. N. et al. 1998; Proebstel, S. 1993; Kilpatrick, C. W. 2002; Seutin, G. et al. 1991) or simply DMSO (Camacho-Sanchez, M. et al. 2013; Corthals, A. et al. 2015; Robertson, K. M. et al. 2013; Michaud, C. L. et al. 2011; Allen-Hall, A. et al. 2012; Hernandez-Agreda, A. et al.

2018), to our knowledge the contributions of the individual components of DESS to DNA preservation have not been examined systematically.

SUMMARY OF INVENTION

One aspect of the present invention provides a method for preserving a biological tissue, comprising contacting for a period of time at a temperature the biological tissue with an aqueous solution comprising a compound having the structure:

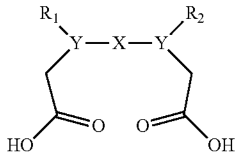

wherein

X is alkyl, alkyl-$X_1$-alkyl, alkyl-$X_1$-alkyl-$X_1$-alkyl, aryl-$X_1$-alkyl-$X_1$-aryl, or $X_2$-alkyl-$X_2$, provided that when X is $X_2$-alkyl-$X_2$, then each Y is CH;

$X_1$, for each occurrence, is independently O, C(H)($R_3$), or $NR_4$;

$X_2$, for each occurrence, is N;

Y, for each occurrence, is independently CH or N;

$R_1$ is —$CO_2H$, -alkyl-OH, or -alkyl-$CO_2H$, provided that when X is $X_2$-alkyl-$X_2$, then when $R_1$ is —$CO_2H$, then the adjacent Y is CH;

$R_2$ is —$CO_2H$, -alkyl-OH, or -alkyl-$CO_2H$, provided that when X is $X_2$-alkyl-$X_2$, then when $R_2$ is —$CO_2H$, then the adjacent Y is CH;

$R_3$ is —OH, —$CO_2H$, or -alkyl-$CO_2H$; and $R_4$ is -alkyl-$CO_2H$.

Another aspect of the present invention provides a method for preserving high molecular weight deoxyribonucleic acid (DNA), comprising contacting for a period of time at a temperature the high molecular weight DNA with an aqueous solution comprising a compound having the structure:

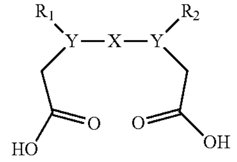

wherein

X is alkyl, alkyl-$X_1$-alkyl, alkyl-$X_1$-alkyl-$X_1$-alkyl, aryl-$X_1$-alkyl-$X_1$-aryl, or $X_2$-alkyl-$X_2$, provided that when X is $X_2$-alkyl-$X_2$, then each Y is CH;

$X_1$, for each occurrence, is independently O, C(H)($R_3$), or $NR_4$;

$X_2$, for each occurrence, is N;

Y, for each occurrence, is independently CH or N;

$R_1$ is —$CO_2H$, -alkyl-OH, or -alkyl-$CO_2H$, provided that when X is $X_2$-alkyl-$X_2$, then when $R_1$ is —$CO_2H$, then the adjacent Y is CH;

$R_2$ is —$CO_2H$, -alkyl-OH, or -alkyl-$CO_2H$, provided that when X is $X_2$-alkyl-$X_2$, then when $R_2$ is —$CO_2H$, then the adjacent Y is CH;

$R_3$ is —OH, —$CO_2H$, or -alkyl-$CO_2H$; and $R_4$ is -alkyl-$CO_2H$.

Another aspect of the present invention provides a method for preserving high molecular weight DNA in biological tissue, comprising contacting for a period of time at a temperature the biological tissue with an aqueous solution comprising a compound having the structure:

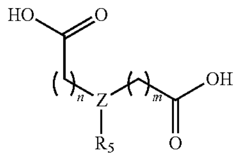

wherein n is 0 or 1;

m is 0 or 1;

Z is present or absent and when present is N or $CR_6$;

$R_5$ is alkyl, —$CO_2H$, -alkyl-OH, or -alkyl-$CO_2H$, provided that when $R_5$ is —$CO_2H$, then Z is $CR_6$; and $R_6$ is —H or —OH.

A further aspect of the present invention provides a method for preserving high molecular weight deoxyribonucleic acid (DNA), comprising contacting for a period of time at a temperature the high molecular weight DNA with an aqueous solution comprising a compound having the structure:

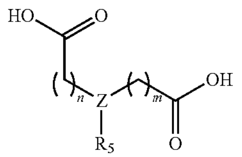

wherein n is 0 or 1;

m is 0 or 1;

Z is present or absent and when present is N or $CR_6$;

$R_5$ is alkyl, —$CO_2H$, -alkyl-OH, or -alkyl-$CO_2H$, provided that when $R_5$ is —$CO_2H$, then Z is $CR_6$; and $R_6$ is —H or —OH.

BRIEF DESCRIPTION OF THE DRAWINGS

FIG. 4: Summary of statistical model results. Percent high molecular weight DNA recovered (% R) and normalized high molecular weight DNA yield (nY). Significant p values ($p<0.05$) indicated with *; df, degrees of freedom.

FIG. 8: Average values for yield (μg), total normalized DNA yield (μg DNA/mg tissue), normalized high molecular weight DNA yield (nY; μg DNA/mg tissue) and percent high molecular weight DNA recovered (% R). Average % R (avg) and standard deviation (SD) for tissues of *Mytilus edulis, Faxonius virilis* and *Alitta virens* extracted immediately after dissection (fresh) or stored for one day (1 d), three months (3 m) or six months (6 m) in preservative treatments containing DMSO (D), EDTA (E) and/or saturated NaCl (SS) or 95% ethanol (EtOH).

FIG. 9: Average high molecular weight DNA recovered. Average % R (avg) and standard deviation (SD) for tissue of *Mytilus edulis, Faxonius virilis*, and *Alitta vixens* extracted immediately after euthanasia (fresh) or stored for one day (1 d), three months (3 m) or six months (6 m) in preservative treatments containing DMSO (D), EDTA (E) and/or saturated NaCl (SS) or 95% ethanol (EtOH). Dashes indicate treatments determined to be terminally degraded, i.e. that yielded less than 10% R at an earlier time point and showed no DNA above 10 kb on agarose gels.

DETAILED DESCRIPTION OF THE INVENTION

Figure 1:
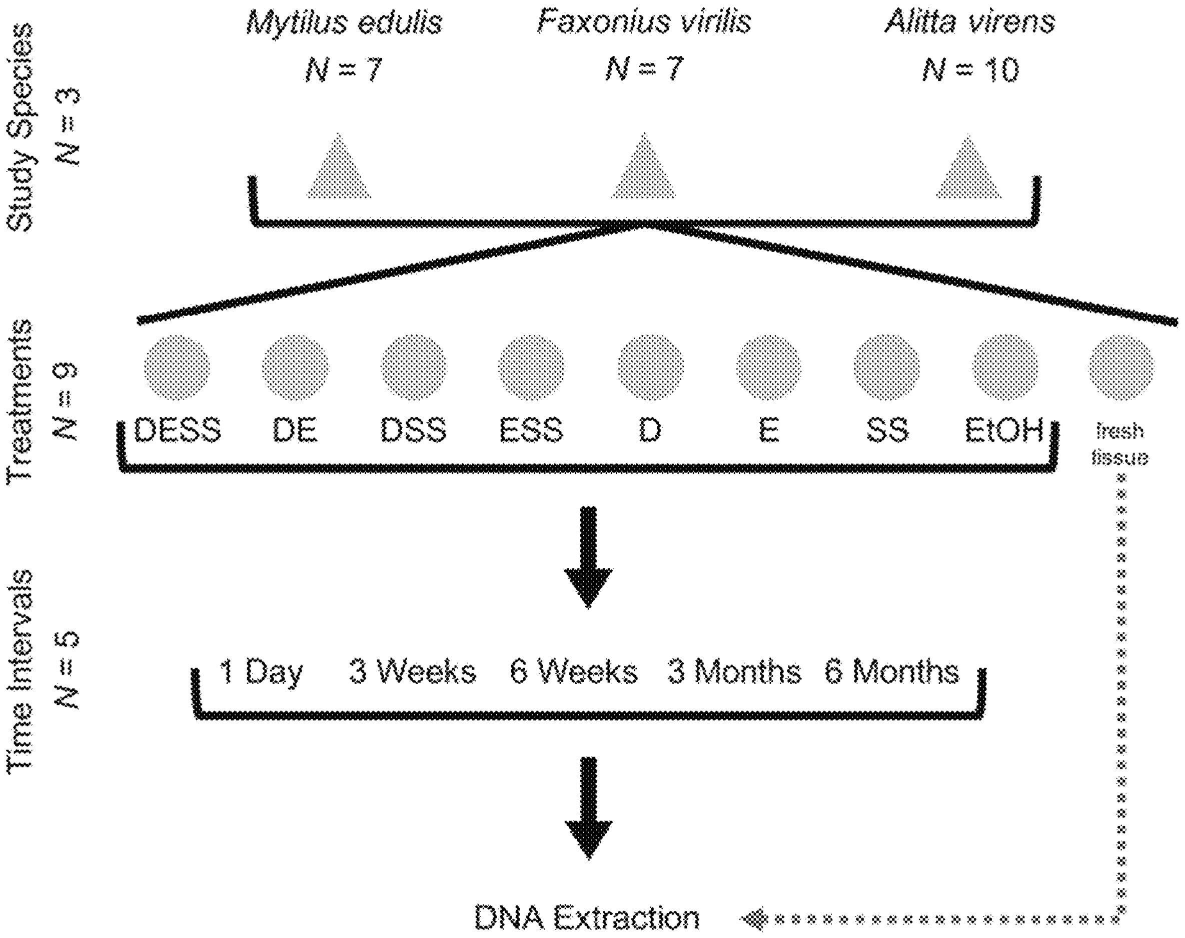
FIG. 1: Seven specimens of *Mytilus edulis*, seven specimens of *Faxonius virilis* and ten specimens of *Alitta virens* were sampled for each time interval. Nine tissue subsamples were collected from each specimen. DNA was extracted from one subsample immediately after dissection without preservation (fresh tissue). Of the remaining eight, one was stored in DESS, one in each of six DESS-variant solutions (DE, DSS, ESS, D, E and SS) and one in 95% EtOH. Separate specimens of each taxon were used for each time interval, for a total of 35 *M. edulis,* 35 *F. virilis* and 50 *A. virens.*

The present invention relates to a tissue preservation method that bypasses the need for dimethyl sulfoxide (DMSO) or other penetrants/solvents and sodium chloride (NaCl) or other salts, and makes the process more widely applicable under various conditions. This method preserves high molecular weight DNA in the tissue by slowing its degradation.

This method is more effective than current agents, e.g. DESS or 95% ethanol. It is also greener and more cost-effective than current agents. In particular, the method is effective at room temperature and does not require low temperatures, e.g. freezing or refrigeration. Also, the compounds used in the present invention require no special handling or safety precautions, e.g. 95% ethanol is highly flammable and subject to shipping restrictions.

EDTA (ethylenediaminetetraacetic acid) with the formula $[CH_2N(CH_2CO_2H)_2]_2$ or a derivative thereof is the active ingredient in the tissue preservation method. Tissue preserved by the method of the present invention can be frozen after treatment without any loss of DNA quality. In fact, the DNA yield and quality is improved when EDTA-preserved tissues are frozen before DNA extraction. This indicates that EDTA may be a desirable routine pretreatment before freezer storage of tissues intended for DNA extraction. Further, tissues treated with EDTA before freezing are resistant to DNA degradation after thawing even after extended periods at room temperature. Therefore, the method of the present invention can be an excellent safeguard against damage to tissues due to freezer failure. Thawing flash frozen tissue in treatment solutions prior to DNA extraction also improves the quality and yield of DNA recovery as compared to extraction of DNA directly from flash frozen tissue.

EDTA or derivatives thereof preserves high molecular weight DNA in the tissue by chelating (trapping) metal ions, including the divalent cation magnesium ($Mg^{2+}$), which is a critical cofactor required by deoxyribonuclease (DNase). EDTA or derivative thereof also chelate a broad range of metals including calcium ($Ca^{2+}$), which can substitute for $Mg^{2+}$ in some DNase molecules, and ferric iron ($Fe^{2+}$), which can enhance natural production of reactive oxygen species (ROS) that may cause oxidative damage to DNA.

EDTA chelates metal ions by forming a cage-like structure in which its four negatively charged carboxyl groups and two nitrogens coordinate with, surround and trap the positively charged metal ion. Thus, it is effective as a hexadentate chelating agent in its tetra-anionic form. The pKa values of the four ionizable carboxyl groups in EDTA are 2.0, 2.7, 6.16, and 10.26, indicating that at pH 10.26, one half of the EDTA molecules in solution are in the tetra-anionic form. The pH of the protonated nitrogen in EDTA is 1.5. Therefore, as the pH of EDTA-containing solutions are raised from pH 8, the pH of DESS, to pH 10, the concentration of the tetra-anionic form of EDTA increases exponentially and the capacity of the solution to chelate $Mg^{2+}$ increases proportionately. Accordingly, the preservation method is improved at higher pH.

EDTA treatment does not interfere with common DNA extraction protocols and does not inhibit the activity of Proteinase K, the most common protease used in DNA extractions. Also, DNA extractions can be performed on tissues preserved in EDTA without need for removing the preservative solution, as is typically necessary for other preservatives.

DNA is soluble in EDTA solutions. This may be advantageous when the intent is to extract the entire sample including the preservative solution, e.g., when extracting DNA from EDTA-preserved blood or body fluids, or when a tissue has been homogenized in an EDTA solution. However, because DNA is soluble in EDTA solutions, DNA may leak from tissues into the preservative fluid, reducing yield from the tissue. While the leaked DNA can be recovered from solution, this require an additional step(s).

Leakage of DNA from tissues can be eliminated by addition an additive to the solution which contacts the tissue, e.g., alcohol(s), that reduce the solubility of the DNA. It was observed that addition of up to 50% EtOH to EDTA solution does not negatively affect preservation of high molecular weight DNA and decreases the solubility of high molecular weight DNA sufficiently to prevent leakage of DNA into the preservative fluid. As an added benefit, EtOH partially dehydrates tissues, often making them more solid and easier to handle.

EtOH (95%) by itself is the most common tissue preservative used when subsequent extraction of DNA is required. It has been shown that in most instances EDTA solutions outperform 95% EtOH for this purpose while avoiding the high flammability and shipping restrictions associated with EtOH (Sarhpe, A. et al. 2020). Combinations of EDTA and EtOH combine the advantages of each preservative while reducing their individual shortcomings.

Definitions

The term "high molecular weight deoxyribonucleic acid (DNA)" or "HMW DNA" as used herein refers to DNA fragments greater than 10 kb in length.

The term "biological tissue" or "tissue" as used herein refers to any type of tissue found in living organisms including connective tissue, epithelial tissue, muscle tissue, and nervous tissue. The term also includes "soft biological tissue" or "soft tissue", e.g. muscle, tendons, ligaments, fat, fibrous tissue, skin, lymph and blood vessels, fasciae, and synovial membranes, and "hard biological tissue" or "hard tissue", e.g. bone, tooth enamel, dentin, and cementum.

The term "extraction" as used herein refers to any method by which DNA or high molecular weight (DNA) is collected from biological tissue including, but not limited to, silica-based DNA extraction, organic extraction or selective precipitation.

EDTA (ethylenediaminetetraacetic acid) and derivatives disclosed here, e.g. HDTA (hydroxyethylethylenediamintriacetic acid), EGTA (ethylene glycol-bis(2-aminoethylether)-N,N,N',N'-tetraacetic acid), and DTPA (diethylenetriaminepentaacetic acid), are commercially available.

"Alkyl" refers to a fully saturated cyclic or acyclic, branched or unbranched carbon chain moiety having the number of carbon atoms specified, or up to 30 carbon atoms if no specification is made. For example, alkyl of 1 to 8 carbon atoms refers to moieties such as methyl, ethyl, propyl, butyl, pentyl, hexyl, heptyl, and octyl, and those moieties which are positional isomers of these moieties. Alkyl of 10 to 30 carbon atoms includes decyl, undecyl, dodecyl, tridecyl, tetradecyl, pentadecyl, hexadecyl, heptadecyl, octadecyl, nonadecyl, eicosyl, heneicosyl, docosyl, tricosyl and tetracosyl. In certain embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. Alkyl groups may be substituted or unsubstituted.

The term "aryl" as used herein includes 3- to 12-membered substituted or unsubstituted single-ring aromatic groups in which each atom of the ring is carbon (i.e., carbocyclic aryl) or where one or more atoms are heteroatoms (i.e., heteroaryl). Preferably, aryl groups include 5- to 12-membered rings, more preferably 6- to 10-membered rings The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Carboycyclic aryl groups include benzene, naphthalene, phenanthrene, phenol, aniline, and the like. Heteroaryl groups include substituted or unsubstituted aromatic 3- to 12-membered ring structures, more preferably 5- to 12-membered rings, more preferably 5- to 10-membered rings, whose ring structures include one to four heteroatoms. Heteroaryl groups include, for example, pyrrole, furan, thiophene, imidazole, oxazole, thiazole, triazole, pyrazole, pyridine, pyrazine, pyridazine and pyrimidine, and the like. Aryl and heteroaryl can be monocyclic, bicyclic, or polycyclic.

Exemplary Embodiments of the Invention

One aspect of the present invention provides a method for preserving high molecular weight DNA in biological tissue, comprising contacting for a period of time at a temperature the biological tissue with an aqueous solution comprising a compound having the structure:

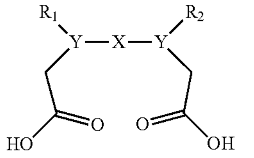

wherein

X is alkyl, alkyl-$X_1$-alkyl, alkyl-$X_1$-alkyl-$X_1$-alkyl, aryl-$X_1$-alkyl-$X_1$-aryl, or $X_2$-alkyl-$X_2$, provided that when X is $X_2$-alkyl-$X_2$, then each Y is CH;

$X_1$, for each occurrence, is independently O, C(H)($R_3$), or $NR_4$;

$X_2$, for each occurrence, is N;

Y, for each occurrence, is independently CH or N;

$R_1$ is —$CO_2H$, -alkyl-OH, or -alkyl-$CO_2H$, provided that when X is $X_2$-alkyl-$X_2$, then when $R_1$ is —$CO_2H$, then the adjacent Y is CH;

$R_2$ is —$CO_2H$, -alkyl-OH, or -alkyl-$CO_2H$, provided that when X is $X_2$-alkyl-$X_2$, then when $R_2$ is —$CO_2H$, then the adjacent Y is CH;

$R_3$ is —OH, —$CO_2H$, or -alkyl-$CO_2H$; and $R_4$ is -alkyl-$CO_2H$.

In certain embodiments, the aqueous solution consists essentially of the compound. In other embodiments, the aqueous solution consists of the compound.

In certain embodiments, the biological tissue is mammalian tissue, arthropod tissue, amphibian tissue, bivalve tissue, or fish tissue.

In certain embodiments, the pH of the aqueous solution is about 8 to 10, e.g. the pH of the aqueous solution is about 8, the pH of the aqueous solution is about 9, or the pH of the aqueous solution is about 10.

In certain embodiments, the concentration of the compound in the aqueous solution is about 0.1-1 M, e.g. the concentration of the compound in the aqueous solution is about 0.25 M or the concentration of the compound in the aqueous solution is about 0.5 M.

In certain embodiments, the aqueous solution further comprises an additive.

In certain embodiments, the additive is ethanol.

In certain embodiments, the additive is methanol or isopropanol.

In certain embodiments, the additive is a salt, e.g. calcium chloride, magnesium chloride, or sodium bicarbonate.

In certain embodiments, the aqueous solution comprises ethanol and water in a ratio of 1:1. In other embodiments, the solution comprises ethanol and water in a ratio of 1:3.

In certain embodiments, the aqueous solution does not comprise dimethyl sulfoxide (DMSO). In other embodiments, the aqueous solution does not comprise sodium chloride (NaCl).

In certain embodiments, the aqueous solution does not comprise dimethyl sulfoxide (DMSO) or contain sodium chloride (NaCl).

In certain embodiments, the period of time is at least 1 day to 6 months. In other embodiments, the period of time is at least 3 months. In other embodiments, the period of time is at least 6 months. In other embodiments, the period of time is at least 12 months.

In certain embodiments, the temperature is room temperature.

In certain embodiments, the high molecular weight DNA is preserved through a freeze-thaw cycle.

Another aspect of the present invention provides a method for preserving high molecular weight deoxyribonucleic acid (DNA), comprising contacting for a period of time at a temperature the high molecular weight DNA with an aqueous solution comprising a compound having the structure:

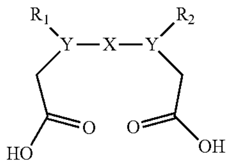

wherein

X is alkyl, alkyl-$X_1$-alkyl, alkyl-$X_1$-alkyl-$X_1$-alkyl, aryl-$X_1$-alkyl-$X_1$-aryl, or $X_2$-alkyl-$X_2$, provided that when X is $X_2$-alkyl-$X_2$, then each Y is CH;

$X_1$, for each occurrence, is independently O, C(H)($R_3$), or $NR_4$;

$X_2$, for each occurrence, is N;

Y, for each occurrence, is independently CH or N;

$R_1$ is —$CO_2H$, -alkyl-OH, or -alkyl-$CO_2H$, provided that when X is $X_2$-alkyl-$X_2$, then when $R_1$ is —$CO_2H$, then the adjacent Y is CH;

$R_2$ is —$CO_2H$, -alkyl-OH, or -alkyl-$CO_2H$, provided that when X is $X_2$-alkyl-$X_2$, then when $R_2$ is —$CO_2H$, then the adjacent Y is CH;

$R_3$ is —OH, —$CO_2H$, or -alkyl-$CO_2H$; and $R_4$ is -alkyl-$CO_2H$.

In certain embodiments, the aqueous solution consists essentially of the compound. In other embodiments, the aqueous solution consists of the compound.

In certain embodiments, the high molecular weight DNA is in biological tissue.

In certain embodiments, the high molecular weight DNA is in mammalian tissue, arthropod tissue, amphibian tissue, bivalve tissue, or fish tissue.

In certain embodiments, the pH of the aqueous solution is about 8 to 10, e.g. the pH of the aqueous solution is about 8, the pH of the aqueous solution is about 9, or the pH of the aqueous solution is about 10.

In certain embodiments, the concentration of the compound in the aqueous solution is about 0.1-1 M, e.g. the concentration of the compound in the aqueous solution is about 0.25 M or the concentration of the compound in the aqueous solution is about 0.5 M.

In certain embodiments, the aqueous solution further comprises an additive.

In certain embodiments, the additive is ethanol.

In certain embodiments, the additive is methanol or isopropanol.

In certain embodiments, the additive is a salt, e.g. calcium chloride, magnesium chloride, or sodium bicarbonate.

In certain embodiments, the aqueous solution comprises ethanol and water in a ratio of 1:1. In other embodiments, the solution comprises ethanol and water in a ratio of 1:3.

In certain embodiments, the aqueous solution does not comprise dimethyl sulfoxide (DMSO). In other embodiments, the aqueous solution does not comprise sodium chloride (NaCl).

In certain embodiments, the aqueous solution does not comprise dimethyl sulfoxide (DMSO) or contain sodium chloride (NaCl).

In certain embodiments, the period of time is at least 1 day to 6 months. In other embodiments, the period of time is at least 3 months. In other embodiments, the period of time is at least 6 months. In other embodiments, the period of time is at least 12 months.

In certain embodiments, the temperature is room temperature.

In certain embodiments, the high molecular weight DNA is preserved through a freeze-thaw cycle.

Another aspect of the present invention provides a method for stabilizing high molecular weight deoxyribonucleic acid (DNA) in biological tissue comprising contacting the biological tissue for a period of time at a temperature with an aqueous solution comprising a compound having the structure:

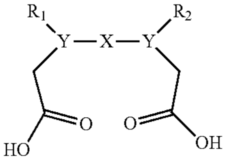

wherein

X is alkyl, alkyl-$X_1$-alkyl, alkyl-$X_1$-alkyl-$X_1$-alkyl, aryl-$X_1$-alkyl-$X_1$-aryl, or $X_2$-alkyl-$X_2$, provided that when X is $X_2$-alkyl-$X_2$, then each Y is CH;

$X_1$, for each occurrence, is independently O, C(H)($R_3$), or $NR_4$;

$X_2$, for each occurrence, is N;

Y, for each occurrence, is independently CH or N;

$R_1$ is —$CO_2H$, -alkyl-OH, or -alkyl-$CO_2H$, provided that when X is $X_2$-alkyl-$X_2$, then when $R_1$ is —$CO_2H$, then the adjacent Y is CH;

$R_2$ is —$CO_2H$, -alkyl-OH, or -alkyl-$CO_2H$, provided that when X is $X_2$-alkyl-$X_2$, then when $R_2$ is —$CO_2H$, then the adjacent Y is CH;

$R_3$ is —OH, —$CO_2H$, or -alkyl-$CO_2H$; and $R_4$ is -alkyl-$CO_2H$.

In certain embodiments, the solution consists essentially of the compound. In other embodiments, the solution consists of the compound.

In certain embodiments of any of the above methods, the compound inhibits growth of microorganisms in the tissue, thereby preserving the tissue.

In certain embodiments of any of the above methods, the compound inhibits growth of bacteria in the tissue, thereby preserving the tissue.

In certain embodiments of any of the above methods, the tissue is characterized by high deoxyribonuclease activity, e.g. human pancreatic tissue.

In certain embodiments, the compound used in any of the above methods has the structure:

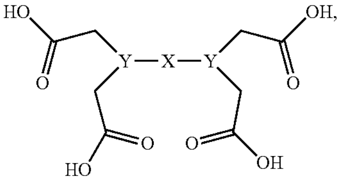

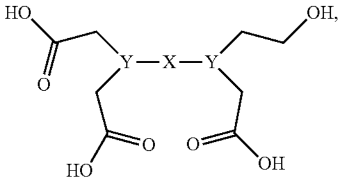 or

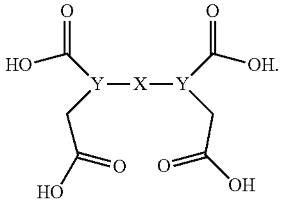

In certain embodiments, each Y is N.

In certain embodiments, X is alkyl, e.g. $CH_2CH_2$, $CH_2CH_2CH_2$, $CH_2C(H)(CH_3)$, or $CH_2CH_2CH_2CH_2CH_2CH_2$.

In certain embodiments, X is alkyl-$X_1$-alkyl, e.g. X is $CH_2CH_2$—$X_1$—$CH_2CH_2$.

In certain embodiments, $X_1$ is O. In other embodiments, $X_1$ is C(H)($R_3$), wherein $R_3$ is —OH. In other embodiments, $X_1$ is $NR_4$, wherein $R_4$ is —$CH_2CO_2H$.

In certain embodiments, X is alkyl-$X_1$-alkyl-$X_1$-alkyl.

In certain embodiments, each $X_1$ is O. In other embodiments, $X_1$ is $NR_4$, wherein $R_4$ is —$CH_2CO_2H$.

In certain embodiments, each alkyl is $CH_2CH_2$.

In certain embodiments, X is aryl-$X_1$-alkyl-$X_1$-aryl.

In certain embodiments, each $X_1$ is O.

In certain embodiments, each aryl is phenyl.

In certain embodiments, wherein the alkyl is $CH_2CH_2$.

In certain embodiments, each Y is CH.

In certain embodiments, X is $X_2$-alkyl-$X_2$

In certain embodiments, $X_2$ is N.

In certain embodiments, the alkyl is $CH_2CH_2$.

In certain embodiments, $R_1$ and $R_2$ are each —$CH_2CO_2H$. In other embodiments, $R_1$ and $R_2$ are each —$CO_2H$. In other embodiments, $R_1$ is $CH_2OH$; and $R_2$ is —$CH_2CO_2H$.

In certain embodiments, the compound used in any of the above methods has the structure:

(EDTA)

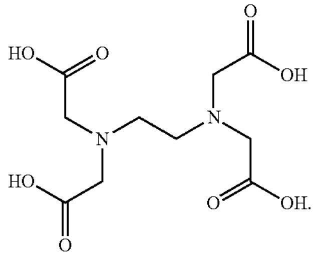

EDTA, alone, is an effective preservative of biological tissue. Derivatives of EDTA, including but not limited to those recited below are also effective in the preservation method:

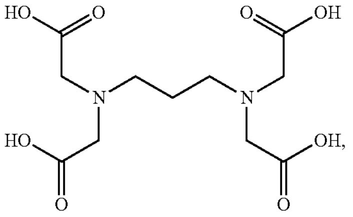

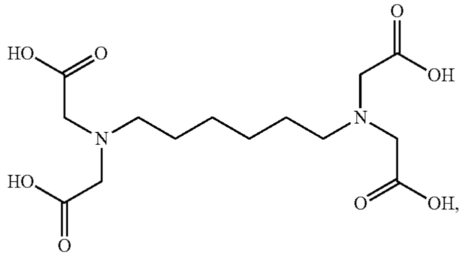

-continued

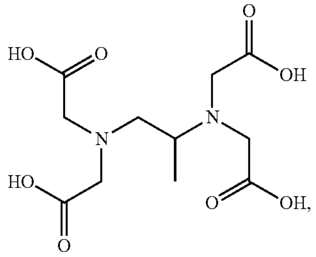

(DPTA-OH)

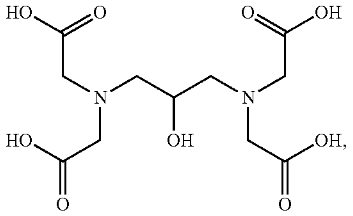

(DTPA)

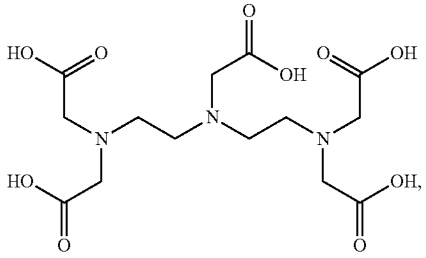

(EGTA)

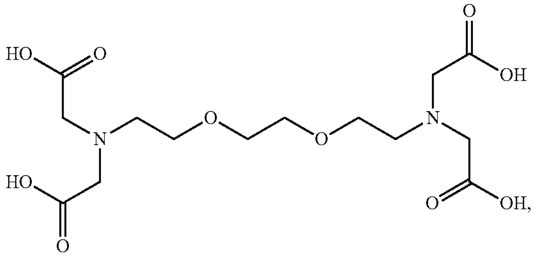

(TTHA)

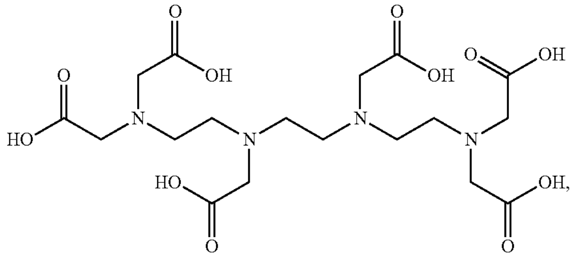

(BAPTA)

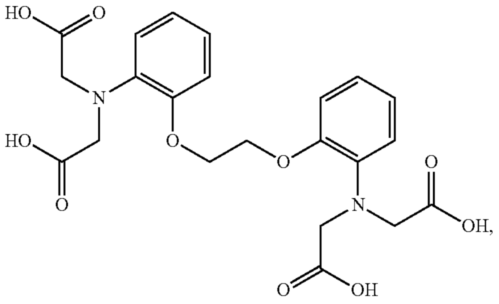

-continued (EDDS)

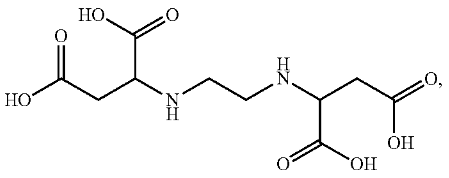

or (HEDTA)

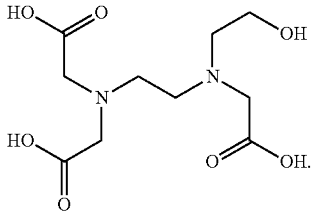

The compound having the following structure is also effective in any of the above preservation methods:

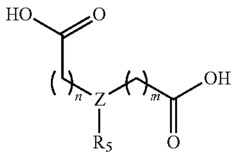

wherein n is 0 or 1;

m is 0 or 1;

Z is present or absent and when present is N or $CR_6$;

$R_5$ is alkyl, —$CO_2H$, -alkyl-OH, or -alkyl-$CO_2H$, provided that when $R_5$ is —$CO_2H$, then Z is $CR_6$; and $R_6$ is —H or —OH.

In certain embodiments, Z is absent; and n and m are each 0.

In certain embodiments, Z is present; and n and m are each 1.

In certain embodiments, the compound used in any of the above methods has the structure:

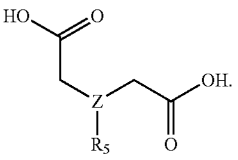

In certain embodiments, Z is N. In other embodiments, Z is $CR_6$.

In certain embodiments, the compound used in any of the above methods has the structure:

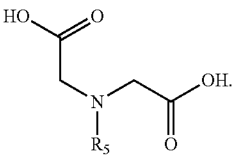

In certain embodiments, $R_5$ is methyl or ethyl. In other embodiments, $R_5$ is —$CH_2CO_2H$.

In certain embodiments, the compound used in any of the above methods has the structure:

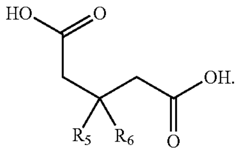

In certain embodiments, $R_5$ is —$CO_2H$. In other embodiments, $R_5$ is —$CH_2CO_2H$.

In certain embodiments, Z is $CR_6$; $R_5$ is —$CO_2H$; and $R_6$ is —OH.

In certain embodiments, the compound used in any of the above methods has the structure:

(citric acid)

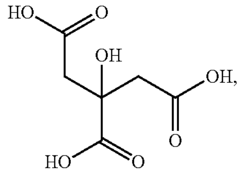

(NTA)

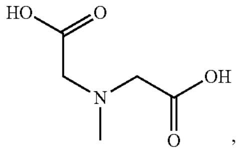

,

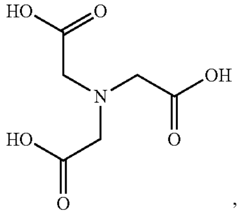

, or (oxalic acid)

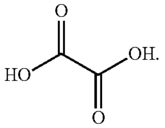

Materials and Methods

To evaluate the contributions of the three components of DESS to DNA preservation in tissues, DNA quality was compared among extracts of tissues from three aquatic invertebrate taxa preserved for various time intervals in DESS or one of six DESS-variant solutions in a full factorial design. Each of these six variants contained either one of the three components of DESS individually or one of the three possible pairwise combinations of two DESS components. When preparing these solutions, DMSO and EDTA were maintained in the same concentrations as they appear in DESS and, when present, NaCl was added to saturation (Table 1). All solutions were prepared at room temperature (22-24° C.) using distilled deionized water as the diluent. Hereafter, we use the following abbreviations to indicate the components of each storage solution: 20% DMSO (D), 0.25 M EDTA (E) and saturated NaCl (SS). In addition, extracts from each of the treatments were compared to those obtained from tissues preserved in 95% EtOH and fresh tissues extracted immediately after specimens were euthanized.

TABLE 1

Tissue storage solutions.

| | Ingredients* | | | |
|---|---|---|---|---|
| | DMSO (ml) | 0.5M EDTA (ml) | NaCl (g)** | EtOH (%) |
| DESS | 100 | 250 | 105 | — |
| DE | 100 | 250 | — | — |
| DSS | 100 | — | 125 | — |
| ESS | — | 250 | 155 | — |
| D | 100 | — | — | — |
| E | — | 250 | — | — |
| SS | — | — | 180 | — |
| ETOH | — | — | — | 95 |

DMSO (D), dimethyl sulfoxide;
EDTA (E), ethylenediaminetetraacetic acid;
NaCl (SS), sodium chloride;
EtOH, ethanol.
*Stocks were diluted to 500 mL final volume with distilled deionized water.
**Approximate quantities required to reach saturation.

Taxon Selection and Sourcing

The three taxa, *Mytilus edulis* Linnaeus (blue mussel; N=35), *Faxonius virilis* Hagan (virile crayfish; N=35) and *Alitta virens* M. Sars (clam worm; N=50) selected for this study represent the common aquatic invertebrate phyla Mollusca, Arthropoda and Annelida, respectively. Previous work by Dawson and our own observations indicated that DESS preserved DNA well in a variety of similar mollusks and arthropods but performed poorly on nereid worms closely related to *A. virens* (Dawson, M. N. et al. 2010). Therefore, the selected taxa likely represent both good and poor use cases for preservation in DESS. *Mytilus edulis* were collected at the Seaport Landing Marina in Lynn, MA (42.45859 N, —70.94275 W) under the Commonwealth of Massachusetts Division of Marine Fisheries Scientific Collection Permit #156386. *Faxonius virilis* were purchased live from A. J.'s Bait & Tackle in Meredith, NH. Live *A. virens* were purchased from Al's Bait and Tackle in Beverly, MA. Samples of all specimens were deposited into the Ocean Genome Legacy Center (OGL) collection and can be accessed using specimen IDs S29192-S29215 and S29350-S29455.

The taxonomic identities of the specimens used in this study were determined by traditional morphology-based methods and confirmed by "DNA barcode" analysis (Hebert, P. D. et al. 2003). The COI barcoding region as identified by Hebert was amplified from DNA extracts of two specimens per taxa using LCO1490_t1: 5'-TGTAAAACGACGG-CCAGTGGTCAACA AATCATAAAGATATTGG-3' (SEQ ID NO: 1) and HCO2198_t2: 5'-CAGGAAACAGC-TATGACTAAA CTTCAGGGTGACCAAAAAATCA-3' (SEQ ID NO: 2) primers (Foottit, R. et al. 2009). Each PCR amplification contained 2 μl DNA template, 17.5 μl OneTaq 2× Master Mix (New England BioLabs; Ipswich, MA), 10 μM of both forward and reverse primers and was brought to 35 μl total volume with deionized water. PCR thermocycler conditions were initiated with a heated lid at 94° C. for 30 seconds, followed by 30 cycles of 94° C. for 30 seconds, 52° C. for 40 seconds and 68° C. for 60 seconds, with a final extension at 68° C. for 5 minutes using a PCT-200 thermocycler (MJ Research, Inc.; Waltham, MA). PCR success was visualized by 1% agarose gel electrophoresis (see details below) and 10 μl of each amplicon was bi-directionally sequenced by the Sanger method on an Applied Biosystems 3730xl DNA Analyzer (Foster City, CA) at a commercial sequencing facility (GENEWIZ, South Plainfield, NJ). Resulting sequences were edited and analyzed using Geneious v.8 (Auckland, New Zealand), automatically trimming ends to remove sequence with greater than a 1% chance of error per base and setting 500 bp as a minimum threshold for a successful read. Assembled contigs were deposited in the Barcode of Life Datasystem (BOLD) under accession numbers DESS001-19 through DESS006-19. Sequence identities to best matches in BOLD are reported in Table 2.

TABLE 2

| OGL Spectrum ID | Record ID of Best Match in BOLD | Species ID of Best Match in BOLD | Sequence Identity (%) |
|---|---|---|---|
| S29192 | ECMOL342-11 | *Mytilus edulis* | 99.21 |
| S29193 | ECMOL335-11 | *Mytilus edulis* | 9.17 |
| S29199 | GBCMD20877-19 | *Faxonius virilis* | 100 |
| S29200 | GBCMD20877-19 | *Faxonius virilis* | 100 |
| S29206 | NBPOL001-08 | *Alitta virens* | 100 |
| S29207 | NBPOL001-08 | *Alitta virens* | 100 |

Dissection and Tissue Sampling

Figure 2A:
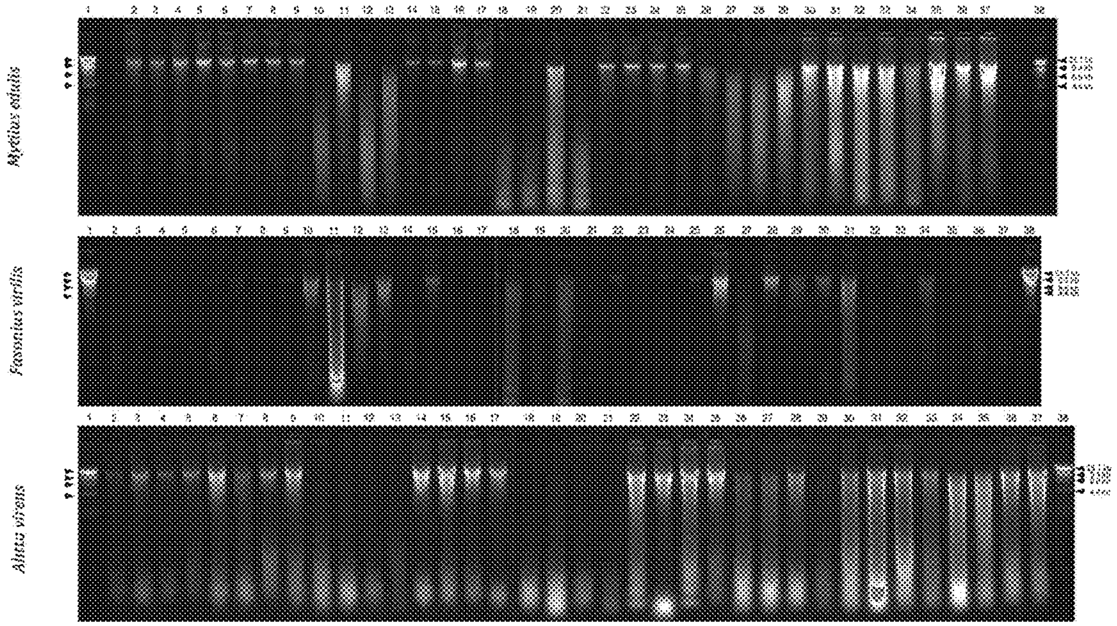
FIG. 2A: Qualitative visualization of DNA fragment size distribution after 1 day by agarose gel electrophoresis. Tissues of three taxa, *Mytilus edulis, Faxonius virilis* and *Alitta virens*, were stored for six months at room temperature in DESS (lanes 2-5), six DESS-variant solutions (DE, lanes 6-9; DSS, lanes 10-13; ESS, lanes 14-17; D, lanes 18-21; E, lanes 22-25; SS, lanes 26-29) and 95% ethanol (lanes 30-33). DNA extracts from fresh tissues are displayed in lanes 34-37. Lanes 1 and 38 contain 0.16 μg of λ DNA- HindIII Digest DNA Ladder (New England BioLabs; Ipswich, MA). D, DMSO; E, EDTA; SS, saturated NaCl; EtOH, 95% ethanol; Fresh, untreated tissue extracted immediately after dissection.
Figure 2B:
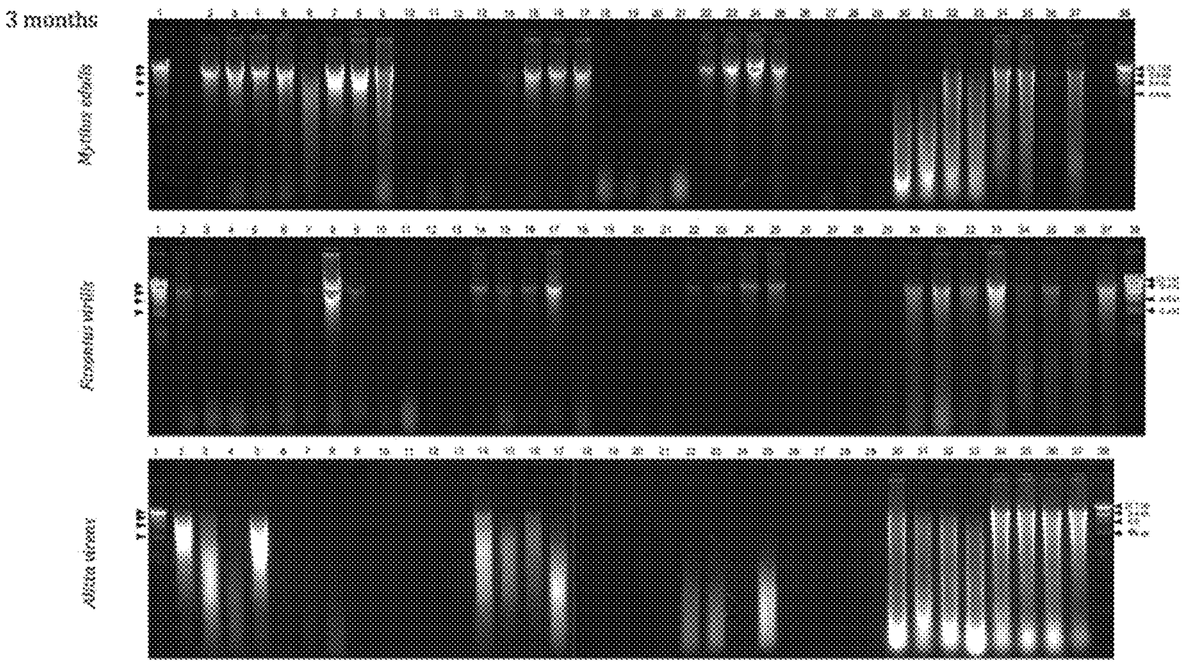
FIG. 2B: Qualitative visualization of DNA fragment size distribution after 3 months by agarose gel electrophoresis. Tissues of three taxa, *Mytilus edulis, Faxonius virilis* and *Alitta virens*, were stored for six months at room temperature in DESS (lanes 2-5), six DESS-variant solutions (DE, lanes 6-9; DSS, lanes 10-13; ESS, lanes 14-17; D, lanes 18-21; E, lanes 22-25; SS, lanes 26-29) and 95% ethanol (lanes 30-33). DNA extracts from fresh tissues are displayed in lanes 34-37. Lanes 1 and 38 contain 0.16 μg of λ DNA-HindIII Digest DNA Ladder (New England BioLabs; Ipswich, MA). D, DMSO; E, EDTA; SS, saturated NaCl; EtOH, 95% ethanol; Fresh, untreated tissue extracted immediately after dissection.

Live specimens of *M. edulis* and *F. virilis* were stored on ice and live *A. virens* were stored at 4° C. prior to dissection. Gill, abdominal muscle and body tissue samples were collected immediately after euthanasia from specimens of *M. edulis, F. virilis*, and *A. virens*, respectively. Nine tissue subsamples of approximately 100 mg (avg. 91.94±24.47 mg) each were collected from each specimen. Eight of the subsamples from each specimen were distributed into 1.8 mL cryotubes each containing either 1 mL of DESS, one of the six DESS-variant solutions or 95% EtOH and were stored at room temperature. DNA was extracted from the ninth subsample, hereafter referred to as fresh tissue, immediately after dissection without preservation. To ensure selection of a time course within which samples could be assessed before reaching an unquantifiable state of degradation, storage intervals of 1 day, 3 weeks, 6 weeks, 3 months and 6 months were chosen (FIG. 1). Gel electrophoresis indicated progressively increasing but qualitatively similar trends of degradation among taxa and treatments with increasing time and showed that high molecular weight DNA could be detected for at least one treatment for all taxa and time intervals examined (FIG. 2). Therefore, the first, middle and last time intervals, 1 day, 3 months and 6 months, were chosen for further qualitative and quantitative analyses. Seven specimens of *M. edulis*, seven specimens of *F. virilis* and ten specimens of *A. virens* were assigned to each time interval for a total of 35 *M. edulis*, 35 *F. virilis* and 50 *A. virens*. Across all treatments, taxa and time intervals, a total of 1,080 samples were analyzed, including 315 samples from *M. edulis*, 315 samples from *F. virilis* and 450 samples from *A. virens*.

DNA Extraction and Quantification

After the assigned storage interval, each tissue sample was removed from its storage solution and reweighed. A tissue subsample of approximately 30 mg (avg. 29.16±4.34 mg) was then excised for DNA extraction. To control for changes in tissue weight during storage, a correction ratio was calculated by dividing the tissue weight prior to storage by the post storage weight. Each extract subsample weight was then multiplied by the correction ratio to estimate the fresh tissue weight equivalent for that subsample. These values were then used to calculate normalized yield (see statistical analysis). DNA was extracted from tissues using the DNeasy Blood and Tissue Kit (Qiagen; Hilden, Germany) following the manufacturers recommended protocol with tissues digested overnight and DNA eluted by adding two sequential 50 μl volumes of Buffer AE for a total elution volume of 100 μl. DNA was extracted from the ninth fresh tissue subsample immediately after dissection by excising and weighing tissue and placing it directly into the digestion solution.

The presence of high molecular weight DNA in each extract was determined qualitatively by agarose gel electrophoresis and quantitatively using an Agilent Technologies TapeStation 2200 DNA Analyzer (Santa Clara, CA). For agarose gel electrophoresis, 3 μl (avg. 0.27±0.70 μg) of each DNA extract was loaded on a 20 cm horizontal slab gel (1% agarose, 1×TAE buffer containing 1% GelRed nucleic acid gel stain (Biotium; Fremont, CA)) and separated at approximately 3 v/cm for 60 minutes and then visualized using a BioRad Gel Doc XR+ Molecular Imager and Image Lab software (Hercules, CA). The first and last lane of each gel was loaded with 1.5 μl of λ DNA-HindIII Digest DNA Ladder (500 μg/ml; New England BioLabs; Ipswich, MA) as a molecular weight standard. Quantitative analyses were performed on 1 μl (avg. 0.09±0.23 μg) of DNA extracts from the 1 day, 3 month and 6 month time intervals using the Agilent DNA Analyzer genomic DNA ScreenTapes and TapeStation Analysis Software (V.A.02.02 (SR1)) to determine both the percent recovery (% R) and normalized yield (nY) of high molecular weight DNA. Additionally, 2 μl (avg. 0.18±0.46 μg) of each sample were analyzed using a Nanodrop 1000 droplet spectrophotometer (Thermo Fisher Scientific; Waltham, MA) to estimate DNA purity using the absorbance ratio at A260/A280.

To evaluate their equivalence with respect to PCR amplification and sequencing, the barcode region of the mitochondrial COI gene was amplified and sequenced from three randomly selected DNA extracts from fresh tissues and tissues stored for 6 months in DESS and E, as described above.

Statistical Analysis

The percentage of high molecular weight DNA recovered (% R) was calculated using data obtained from the Agilent Technologies TapeStation 2200 DNA Analyzer as follows:

$$\%\ R = \frac{ng/\mu l\ HMW\ DNA(>10\,kb)}{ng/\mu l\ \text{total}\,DNA} \times 100\%$$

Normalized high molecular weight DNA yield (nY) was calculated as follows using data obtained from the Agilent Technologies TapeStation 2200 DNA Analyzer and extract tissue weights modified by the correction ratio explained above:

$$nY = \frac{\mu g\ HMW\ DNA(>10\ kb)}{\text{mg extract tissue weight} \times \text{correction ratio}}$$

Data for each taxon, time interval and response variable (% R and nY) were analyzed separately. A Shapiro-Wilk normality test was used to determine whether data were normally distributed. For each taxon, the effect of storage solution on DNA quality was assessed using a repeated measures design: normally distributed data were analyzed using a parametric repeated measures ANOVA and non-normal data were analyzed using a non-parametric Friedman $\chi 2$ test (RStudio v. 1.2.1335). Post-hoc tests for repeated measures ANOVAs were performed with the 'nlme' package in RStudio (Version 3.1-137). We used the Friedman Conover test as a post-hoc test for Friedman $\chi 2$ analyses and performed them with a Bonferroni correction in the 'PMCMR' package (Version 4.3).

DNA was recovered from all samples, taxa, treatments and storage intervals, with the exception of two *A. virens* samples (DESS, 6 months and DE, 6 months), which were lost during DNA extraction. To maintain a fully crossed experiment, all samples derived from these two specimens were excluded from statistical analyses but were included when reporting summary statistics. Total normalized DNA yields ranged from 0.0007 to 12.80 μg DNA/mg tissue and % R ranged from 0.14 to 66.76% across all taxa, treatments and time intervals.

Example 1. Qualitative Analysis of DNA Fragment Length Distribution

Figure 3:
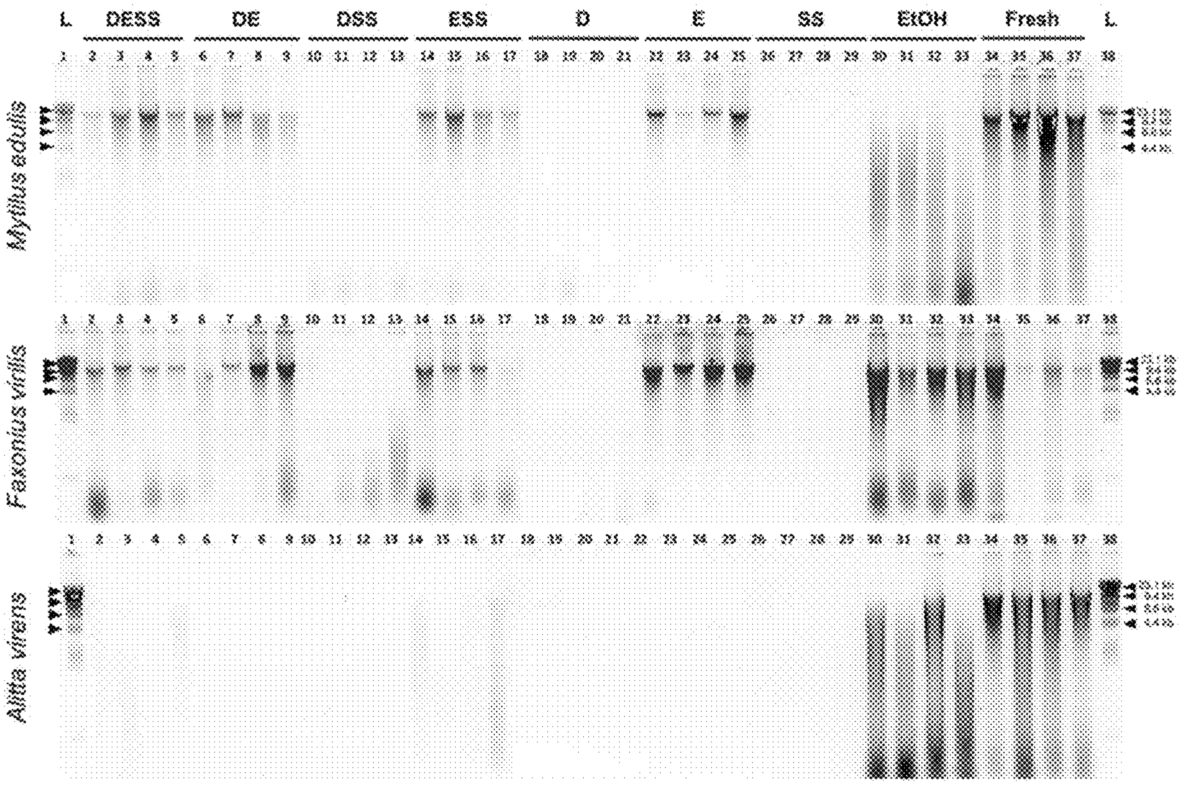
FIG. 3: Qualitative visualization of DNA fragment size distribution after 6 months by agarose gel electrophoresis. Tissues of three taxa, *Mytilus edulis, Faxonius virilis* and *Alitta virens*, were stored for six months at room temperature in DESS (lanes 2-5), six DESS-variant solutions (DE, lanes 6-9; DSS, lanes 10-13; ESS, lanes 14-17; D, lanes 18-21; E, lanes 22-25; SS, lanes 26-29) and 95% ethanol (lanes 30-33). DNA extracts from fresh tissues are displayed in lanes 34-37. Lanes 1 and 38 contain 0.16 μg of λ DNA-HindIII Digest DNA Ladder (New England BioLabs; Ipswich, MA). D, DMSO; E, EDTA; SS, saturated NaCl; EtOH, 95% ethanol; Fresh, untreated tissue extracted immediately after dissection.

Qualitative analysis of DNA fragment length distribution, as visualized by agarose gel electrophoresis, showed a similar pattern for all taxa. Specifically, over the duration of the experiment the apparent quantity of observable high molecular weight DNA declined first in tissues stored in DESS variant solutions that did not contain EDTA (DSS, D and SS). This was evident by one day for tissues of *A. virens* and by 3 months for *M. edulis* and *F. virilis* (FIG. 2). By 6 months, high molecular weight DNA could no longer be visualized in extracts of *M. edulis* and *F. virilis* stored in DESS-variant solutions lacking E (DSS, D and SS) but was evident in all DESS-variant solutions containing E (DESS, ESS and E), as well as in extracts from fresh and EtOH-preserved tissues. For tissues of *A. virens*, by 6 months high molecular weight DNA was no longer observable or appeared only as faint and variable smears in extracts of tissues stored in all DESS-variant solutions (FIG. 3).

Example 2. Quantitative Analyses of DNA Fragment Length Distribution

Figure 5A:
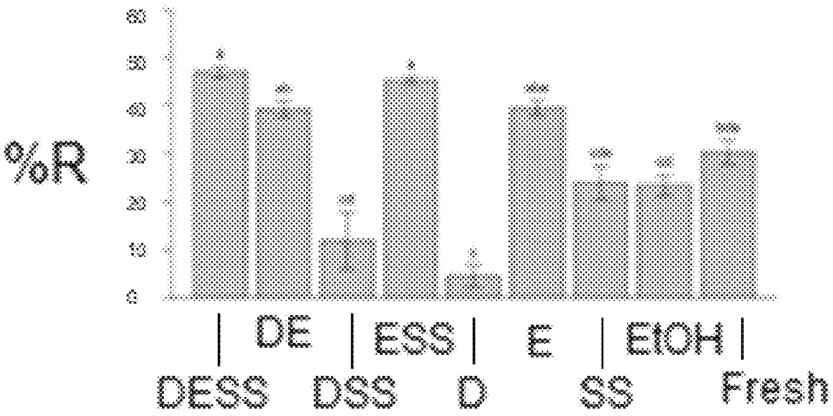
FIG. 5A: Percent high molecular weight DNA recovered. Average percent high molecular weight DNA recovered (% R) was determined for tissues of *Mytilus edulis* extracted immediately from fresh tissue or stored for 1 day at room temperature in DESS, six DESS variant solutions or 95% ethanol. Error bars represent standard error. Within each histogram, treatments bearing different lower-case letters are significantly different at $p<0.05$; matching lower case letters indicate statistically indistinguishable treatments. D, DMSO; E, EDTA; SS, saturated NaCl; EtOH, 95% ethanol; Fresh, untreated tissue extracted immediately after dissection.
Figure 5B:
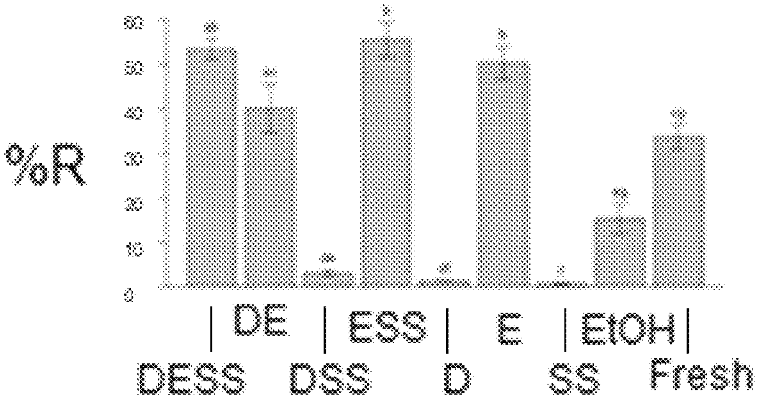
FIG. 5B: Percent high molecular weight DNA recovered. Average percent high molecular weight DNA recovered (% R) was determined for tissues of *Mytilus edulis* extracted immediately from fresh tissue or stored for 3 months at room temperature in DESS, six DESS variant solutions or 95% ethanol. Error bars represent standard error. Within each histogram, treatments bearing different lower-case letters are significantly different at $p<0.05$; matching lower case letters indicate statistically indistinguishable treatments. D, DMSO; E, EDTA; SS, saturated NaCl; EtOH, 95% ethanol; Fresh, untreated tissue extracted immediately after dissection.
Figure 5C:
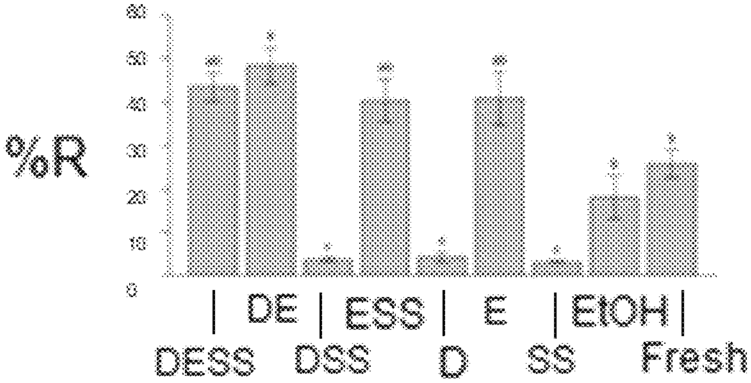
FIG. 5C: Percent high molecular weight DNA recovered. Average percent high molecular weight DNA recovered (% R) was determined for tissues of *Mytilus edulis* extracted immediately from fresh tissue or stored for 6 months at room temperature in DESS, six DESS variant solutions or 95% ethanol. Error bars represent standard error. Within each histogram, treatments bearing different lower-case letters are significantly different at $p<0.05$; matching lower case letters indicate statistically indistinguishable treatments. D, DMSO; E, EDTA; SS, saturated NaCl; EtOH, 95% ethanol; Fresh, untreated tissue extracted immediately after dissection.
Figure 5D:
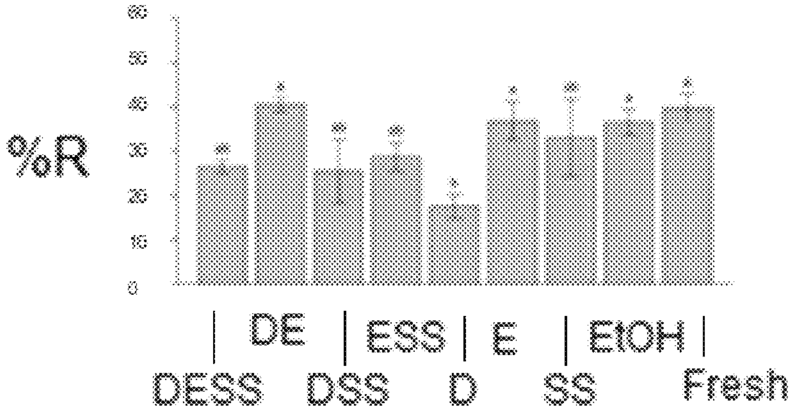
FIG. 5D: Percent high molecular weight DNA recovered. Average percent high molecular weight DNA recovered (% R) was determined for tissues of *Faxonius virilis* extracted immediately from fresh tissue or stored for 1 day at room temperature in DESS, six DESS variant solutions or 95% ethanol. Error bars represent standard error. Within each histogram, treatments bearing different lower-case letters are significantly different at $p<0.05$; matching lower case letters indicate statistically indistinguishable treatments. D, DMSO; E, EDTA; SS, saturated NaCl; EtOH, 95% ethanol; Fresh, untreated tissue extracted immediately after dissection.
Figure 5E:
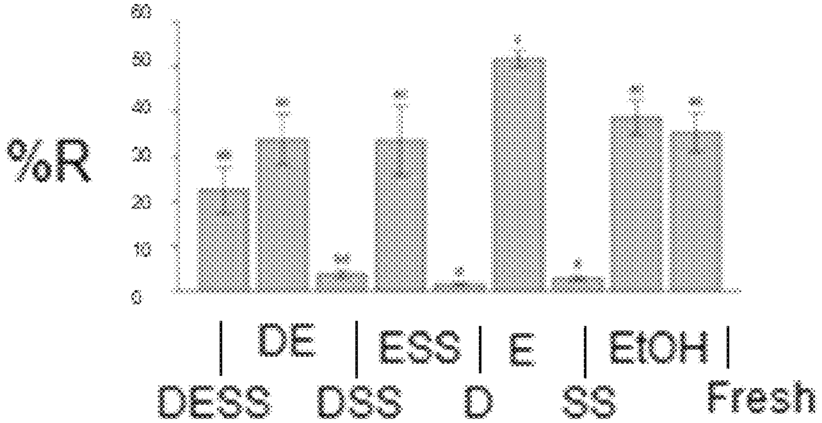
FIG. 5E: Percent high molecular weight DNA recovered. Average percent high molecular weight DNA recovered (% R) was determined for tissues of *Faxonius virilis* extracted immediately from fresh tissue or stored for 3 months at room temperature in DESS, six DESS variant solutions or 95% ethanol. Error bars represent standard error. Within each histogram, treatments bearing different lower-case letters are significantly different at $p<0.05$; matching lower case letters indicate statistically indistinguishable treatments. D, DMSO; E, EDTA; SS, saturated NaCl; EtOH, 95% ethanol; Fresh, untreated tissue extracted immediately after dissection.
Figure 5F:
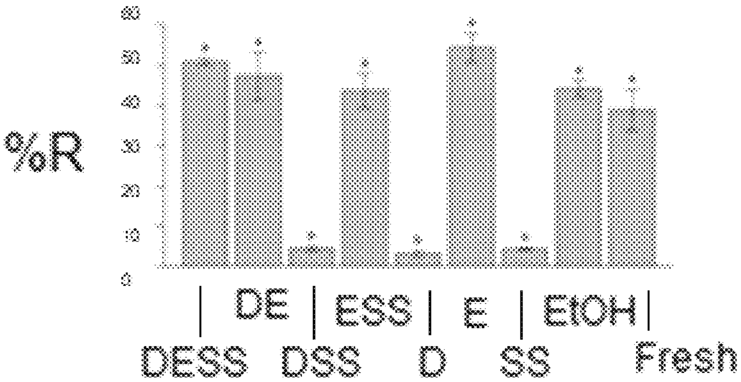
FIG. 5F: Percent high molecular weight DNA recovered. Average percent high molecular weight DNA recovered (% R) was determined for tissues of *Faxonius virilis* extracted immediately from fresh tissue or stored for 6 months at room temperature in DESS, six DESS variant solutions or 95% ethanol. Error bars represent standard error. Within each histogram, treatments bearing different lower-case letters are significantly different at $p<0.05$; matching lower case letters indicate statistically indistinguishable treatments. D, DMSO; E, EDTA; SS, saturated NaCl; EtOH, 95% ethanol; Fresh, untreated tissue extracted immediately after dissection.
Figure 5G:
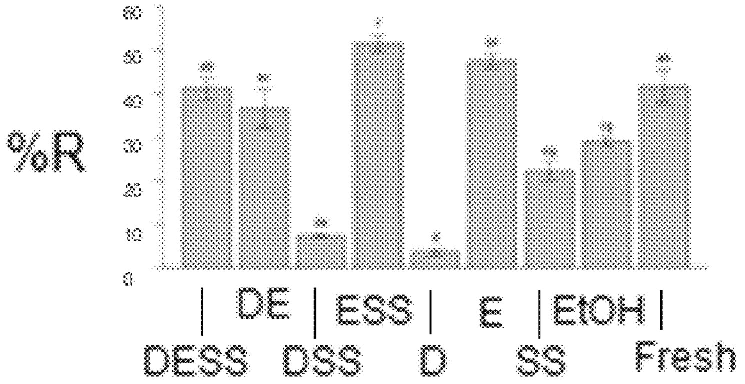
FIG. 5G: Percent high molecular weight DNA recovered. Average percent high molecular weight DNA recovered (% R) was determined for tissues of *Alitta virens* extracted immediately from fresh tissue or stored for 1 day at room temperature in DESS, six DESS variant solutions or 95% ethanol. Error bars represent standard error. Within each histogram, treatments bearing different lower-case letters are significantly different at $p<0.05$; matching lower case letters indicate statistically indistinguishable treatments. D, DMSO; E, EDTA; SS, saturated NaCl; EtOH, 95% ethanol; Fresh, untreated tissue extracted immediately after dissection.
Figure 6A:
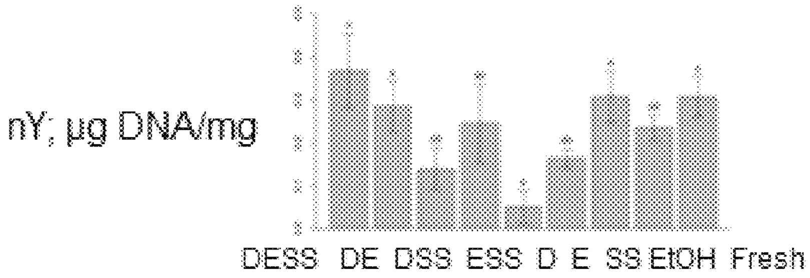
FIG. 6A: Normalized high molecular weight DNA yield. Average normalized high molecular weight DNA yield (nY; μg DNA/mg tissue) was determined for tissues of *Mytilus edulis* extracted immediately from fresh tissue or stored for 1 day at room temperature in DESS, six DESS-variant solutions or 95% ethanol. Error bars represent standard error. Within each histogram, treatments bearing different lower-case letters are significantly different at $p<0.05$; matching lower case letters indicate statistically indistinguishable treatments; an absence of letters indicates no significant difference among all treatments in a given model. Note that y-axis scales differ among taxa and time intervals. D, DMSO; E, EDTA; SS, saturated NaCl; EtOH, 95% ethanol; Fresh, untreated tissue extracted immediately after dissection.
Figure 6B:
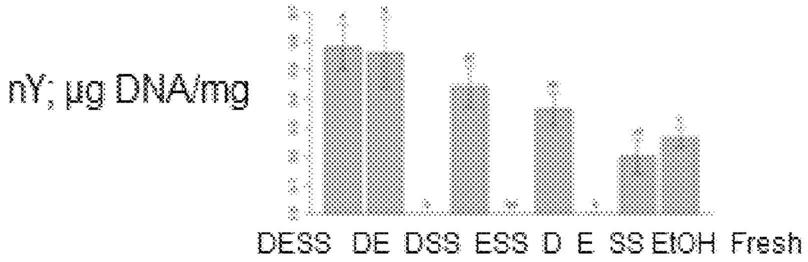
FIG. 6B: Normalized high molecular weight DNA yield. Average normalized high molecular weight DNA yield (nY; μg DNA/mg tissue) was determined for tissues of *Mytilus edulis* extracted immediately from fresh tissue or stored for 3 months at room temperature in DESS, six DESS-variant solutions or 95% ethanol. Error bars represent standard error. Within each histogram, treatments bearing different lower-case letters are significantly different at $p<0.05$; matching lower case letters indicate statistically indistinguishable treatments; an absence of letters indicates no significant difference among all treatments in a given model. Note that y-axis scales differ among taxa and time intervals. D, DMSO; E, EDTA; SS, saturated NaCl; EtOH, 95% ethanol; Fresh, untreated tissue extracted immediately after dissection.
Figure 6C:
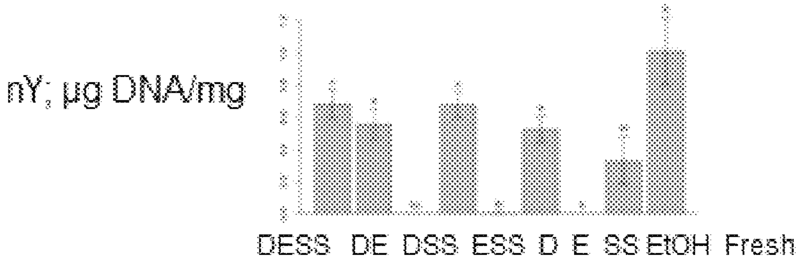
FIG. 6C: Normalized high molecular weight DNA yield. Average normalized high molecular weight DNA yield (nY; μg DNA/mg tissue) was determined for tissues of *Mytilus edulis* that were extracted immediately from fresh tissue or stored for 6 months at room temperature in DESS, six DESS-variant solutions or 95% ethanol. Error bars represent standard error. Within each histogram, treatments bearing different lower-case letters are significantly different at $p<0.05$; matching lower case letters indicate statistically indistinguishable treatments; an absence of letters indicates no significant difference among all treatments in a given model. Note that y-axis scales differ among taxa and time intervals. D, DMSO; E, EDTA; SS, saturated NaCl; EtOH, 95% ethanol; Fresh, untreated tissue extracted immediately after dissection.
Figure 6D:
FIG. 6D: Normalized high molecular weight DNA yield. Average normalized high molecular weight DNA yield (nY; μg DNA/mg tissue) was determined for tissues of *Faxonius virilis* extracted immediately from fresh tissue or stored for 1 day at room temperature in DESS, six DESS-variant solutions or 95% ethanol. Error bars represent standard error. Within each histogram, treatments bearing different lower-case letters are significantly different at $p<0.05$; matching lower case letters indicate statistically indistinguishable treatments; an absence of letters indicates no significant difference among all treatments in a given model. Note that y-axis scales differ among taxa and time intervals. D, DMSO; E, EDTA; SS, saturated NaCl; EtOH, 95% ethanol; Fresh, untreated tissue extracted immediately after dissection.
Figure 6E:
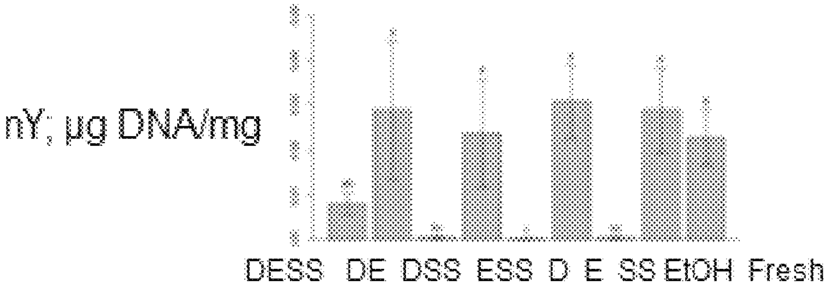
FIG. 6E: Normalized high molecular weight DNA yield. Average normalized high molecular weight DNA yield (nY; μg DNA/mg tissue) was determined for tissues of *Faxonius virilis* extracted immediately from fresh tissue or stored for 3 months at room temperature in DESS, six DESS-variant solutions or 95% ethanol. Error bars represent standard error. Within each histogram, treatments bearing different lower-case letters are significantly different at $p<0.05$; matching lower case letters indicate statistically indistinguishable treatments; an absence of letters indicates no significant difference among all treatments in a given model. Note that y-axis scales differ among taxa and time intervals. D, DMSO; E, EDTA; SS, saturated NaCl; EtOH, 95% ethanol; Fresh, untreated tissue extracted immediately after dissection.
Figure 6F:
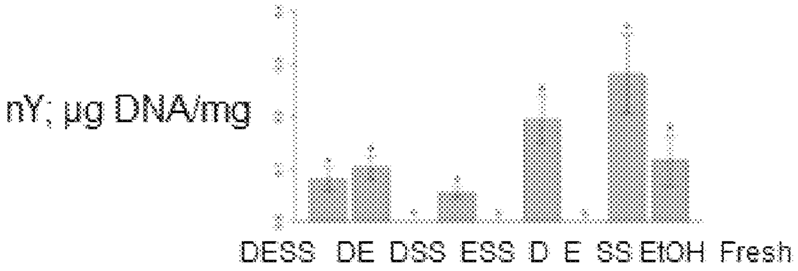
FIG. 6F: Normalized high molecular weight DNA yield. Average normalized high molecular weight DNA yield (nY; μg DNA/mg tissue) was determined for tissues of *Faxonius virilis* that were extracted immediately from fresh tissue or stored for 6 months at room temperature in DESS, six DESS-variant solutions or 95% ethanol. Error bars represent standard error. Within each histogram, treatments bearing different lower-case letters are significantly different at $p<0.05$; matching lower case letters indicate statistically indistinguishable treatments; an absence of letters indicates no significant difference among all treatments in a given model. Note that y-axis scales differ among taxa and time intervals. D, DMSO; E, EDTA; SS, saturated NaCl; EtOH, 95% ethanol; Fresh, untreated tissue extracted immediately after dissection.
Figure 6G:
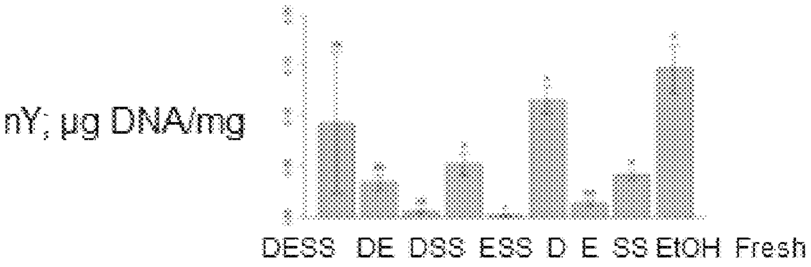
FIG. 6G: Normalized high molecular weight DNA yield. Average normalized high molecular weight DNA yield (nY; μg DNA/mg tissue) was determined for tissues of *Alitta virens* extracted immediately from fresh tissue or stored for 1 day at room temperature in DESS, six DESS-variant solutions or 95% ethanol. Error bars represent standard error. Within each histogram, treatments bearing different lower-case letters are significantly different at $p<0.05$; matching lower case letters indicate statistically indistinguishable treatments; an absence of letters indicates no significant difference among all treatments in a given model. Note that y-axis scales differ among taxa and time intervals. D, DMSO; E, EDTA; SS, saturated NaCl; EtOH, 95% ethanol; Fresh, untreated tissue extracted immediately after dissection.

Quantitative analyses of DNA fragment length distribution were performed using the Agilent Technologies TapeStation 2200 DNA Analyzer. Results for all statistical models appear in FIG. 4. These data revealed statistically significant differences in % R and/or nY among treatment groups for all taxa and time intervals, even after just one day of storage. For example, after one day of storage in solutions D and DSS, tissues of *M. edulis* showed values of % R significantly lower than those for tissues stored in DESS, DE, ESS and E (FIGS. 5A and 9). For this same taxon and time interval, nY values for extracts of tissue stored in solution D were also significantly lower than those of DESS, DE, SS and fresh tissue (FIG. 6A). In the case of *F. virilis*, the % R value for extracts of tissue stored in solution D for one day was significantly lower than those for DE, E, EtOH and fresh tissue (FIGS. 5D and 9). No significant differences in nY were observed among treatments for tissues of *F. virilis* at one day (FIG. 6D). For *A. virens*, all treatments containing EDTA (DESS, DE, ESS and E) yielded % R values equal to or significantly greater than that recovered from fresh tissue at one day, while those lacking EDTA (DSS, D and SS) yielded values significantly lower than fresh tissue (FIGS. 5G and 9). For this taxon and time interval, treatment E performed best with respect to nY, giving values statistically indistinguishable from fresh tissue (FIG. 6G). In contrast, treatments D and DSS performed most poorly, giving nY values significantly lower than all treatments except SS.

At three months, tissues of *M. edulis* maintained in storage solutions without EDTA (DSS, D and SS) yielded significantly lower % R and nY than fresh tissues or any storage solution containing E (DESS, DE, ESS and E). Similarly, in *F. virilis*, tissues stored in solutions without E (DSS, D and SS) yielded a significantly lower % R and nY than fresh tissue or tissues stored in solutions containing E (DESS, DE, ESS and E), with the exception of DESS, which did not differ significantly from either the best or worst treatments. Additionally, tissues from these two taxa stored in any solution containing E (DESS, DE, ESS and E) or EtOH yielded % R and nY values equal to or significantly greater than fresh tissues at 3 months (FIGS. 5B, 5E, 6B, and 6E and 9).

Figure 5H:
FIG. 5H: Percent high molecular weight DNA recovered. Average percent high molecular weight DNA recovered (% R) was determined for tissues of *Alitta virens* extracted immediately from fresh tissue or stored for 3 months at room temperature in DESS, six DESS variant solutions or 95% ethanol. Error bars represent standard error. Within each histogram, treatments bearing different lower-case letters are significantly different at $p<0.05$; matching lower case letters indicate statistically indistinguishable treatments. D, DMSO; E, EDTA; SS, saturated NaCl; EtOH, 95% ethanol; Fresh, untreated tissue extracted immediately after dissection.
Figure 5I:
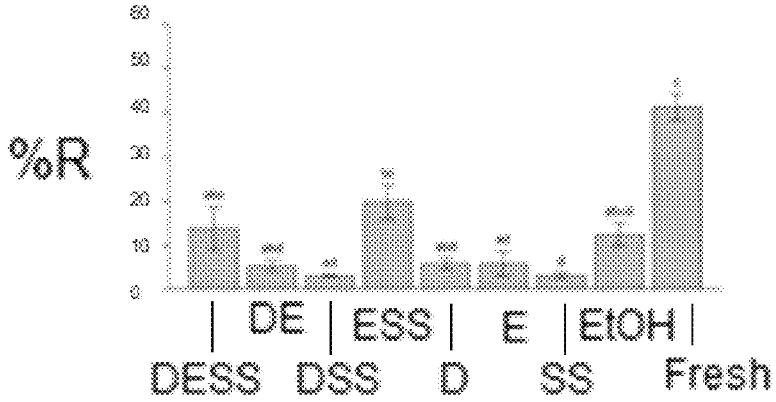
FIG. 5I: Percent high molecular weight DNA recovered. Average percent high molecular weight DNA recovered (% R) was determined for tissues of *Alitta virens* extracted immediately from fresh tissue or stored for 6 months at room temperature in DESS, six DESS variant solutions or 95% ethanol. Error bars represent standard error. Within each histogram, treatments bearing different lower-case letters are significantly different at $p<0.05$; matching lower case letters indicate statistically indistinguishable treatments. D, DMSO; E, EDTA; SS, saturated NaCl; EtOH, 95% ethanol; Fresh, untreated tissue extracted immediately after dissection.
Figure 6H:
FIG. 6H: Normalized high molecular weight DNA yield. Average normalized high molecular weight DNA yield (nY; μg DNA/mg tissue) was determined for tissues of *Alitta virens* extracted immediately from fresh tissue or stored for 3 months at room temperature in DESS, six DESS-variant solutions or 95% ethanol. Error bars represent standard error. Within each histogram, treatments bearing different lower-case letters are significantly different at $p<0.05$; matching lower case letters indicate statistically indistinguishable treatments; an absence of letters indicates no significant difference among all treatments in a given model. Note that y-axis scales differ among taxa and time intervals. D, DMSO; E, EDTA; SS, saturated NaCl; EtOH, 95% ethanol; Fresh, untreated tissue extracted immediately after dissection.
Figure 6I:
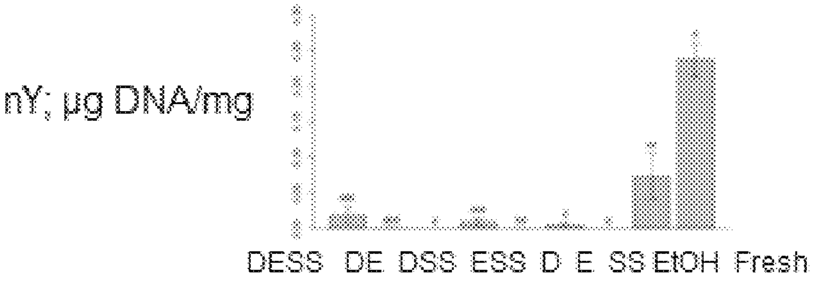
FIG. 6I: Normalized high molecular weight DNA yield. Average normalized high molecular weight DNA yield (nY; μg DNA/mg tissue) was determined for tissues of *Alitta virens* that were extracted immediately from fresh tissue or stored for 6 months at room temperature in DESS, six DESS-variant solutions or 95% ethanol. Error bars represent standard error. Within each histogram, treatments bearing different lower-case letters are significantly different at $p<0.05$; matching lower case letters indicate statistically indistinguishable treatments; an absence of letters indicates no significant difference among all treatments in a given model. Note that y-axis scales differ among taxa and time intervals. D, DMSO; E, EDTA; SS, saturated NaCl; EtOH, 95% ethanol; Fresh, untreated tissue extracted immediately after dissection.

In contrast, % R values for all *A. virens* tissue stored in DESS-variant solutions for 3 months were significantly lower than that for fresh tissue (FIGS. 5H and 9). Nonetheless, A. *virens* tissue stored in DESS, ESS or EtOH were statistically indistinguishable from each other with respect to % R and nY and performed significantly better than tissues preserved in DE, DSS, D and E (FIGS. 5H and 6H). After six months of storage, % R and nY values for tissues of both *M. edulis* and *F. virilis* maintained in storage solutions without EDTA (DSS, D and SS) were significantly lower than those for DESS-variants containing EDTA and for those from fresh tissues. Importantly, for both taxa, % R and nY values for tissues maintained in E-containing storage solutions (DESS, DE, ESS and E) were not significantly different from those of fresh tissues or stored in EtOH, with the exception of DE in *M. edulis*, for which % R values were significantly higher than those for EtOH and fresh tissue (FIGS. 5C, 5F, 6C, and 6F). Finally, for *A. virens*, all treatments, except DESS, ESS and EtOH for % R and ESS and EtOH for nY, yielded values that were significantly lower than those for fresh tissue (FIGS. 5I and 6I).

Figure 7:
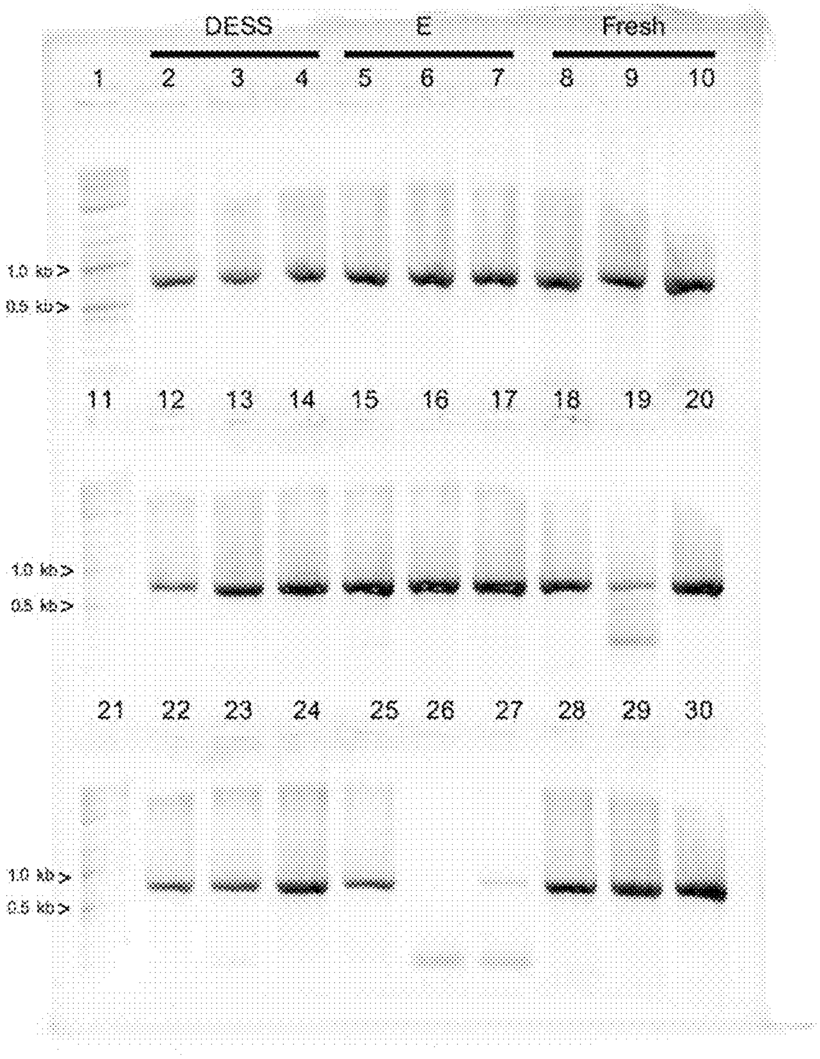
FIG. 7: Select DNA extracts from all three taxa were PCR amplified after storage for six months. *Mytilus edulis* tissues stored in DESS (lanes 2-4), E (lanes 5-7) or fresh (8-10); *Foxonius virilis* tissues stored in DESS (12-14), E (lanes 15-17) or fresh (18-20); *Alitta virens* tissues stored in DESS (lanes 22-24), E (25-27) or fresh (28-30). Lanes 1, 11 and 21 contain 0.05 μg of Quick-Load Purple 1 kb Plus DNA Ladder (New England BioLabs; Ipswich, MA).

As an indicator of DNA utility for downstream applications, PCR amplification and sequencing were performed for three randomly selected individuals from fresh tissue of each taxon and tissues stored for six months in treatments DESS or E. With the exception of 1 sample of *A. virens* stored in E, PCR amplifications produced appropriately sized PCR product bands when visualized on agarose gels (FIG. 7). Despite failing to produce a visible PCR band this sample yielded sufficient product for successful sequencing. Of the 27 samples sent for sequencing, 26 samples gave unidirectional sequence and 24 gave bidirectional sequence of at least 500 bp with >94.4% of all base positions yielding quality scores ≥Q20. The sample that failed to produce usable sequence was from fresh tissue of an individual of *M. edulis*. Of the two samples that did not produce bidirectional reads with sufficient quality, one was *F. virilis* preserved in DESS and the other was *A. virens* preserved in E. Although the resulting sequences differed among individual specimens, as should be expected due to within species variation, identical sequences were observed for all PCR products derived from a given individual, regardless of storage treatment. Sequences have been submitted to BOLD and have the following IDs: DESS007-20-DESS032-20.

Example 3. pH Studies

Figure 10:
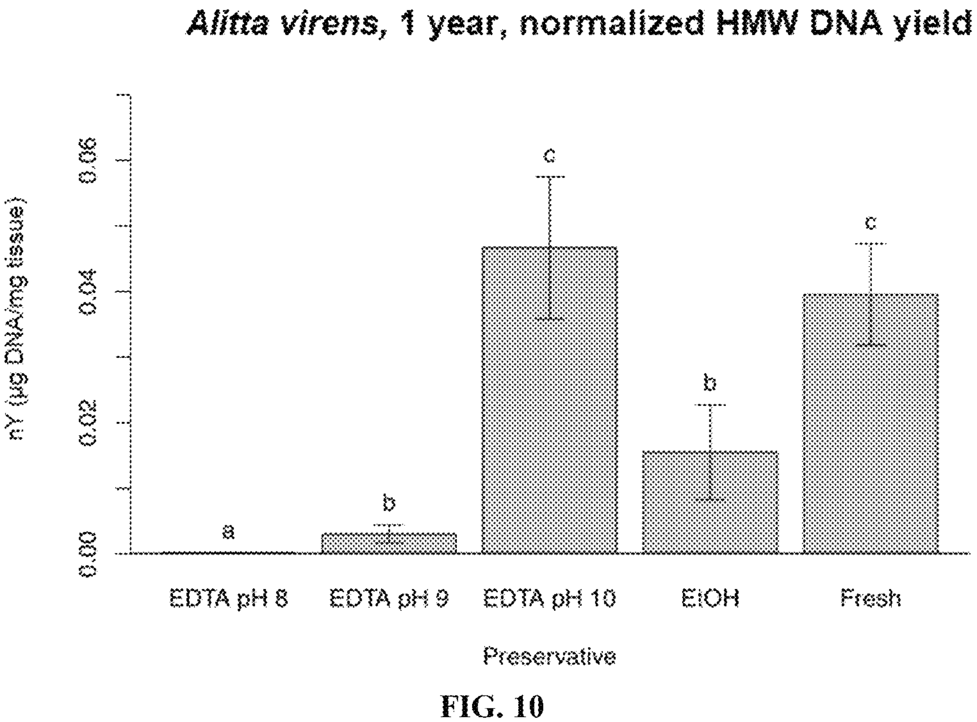
FIG. 10: Normalized high molecular weight DNA yield. Average normalized high molecular weight DNA yield (nY; μg DNA/mg tissue) was determined for tissues of *Alitta virens* extracted immediately from fresh tissue or stored for 1 year at room temperature in 0.25 M EDTA, pH 8.0, 0.25 M EDTA, pH 9.0, 0.25 M EDTA, pH 10.0 and 95% ethanol. Error bars represent standard error. Within each histogram, treatments bearing different lower-case letters are significantly different at $p<0.05$, N=9; matching lower-case letters indicate statistically indistinguishable treatments. EtOH, 95% ethanol; Fresh, untreated tissue extracted immediately after dissection.
Figure 11:
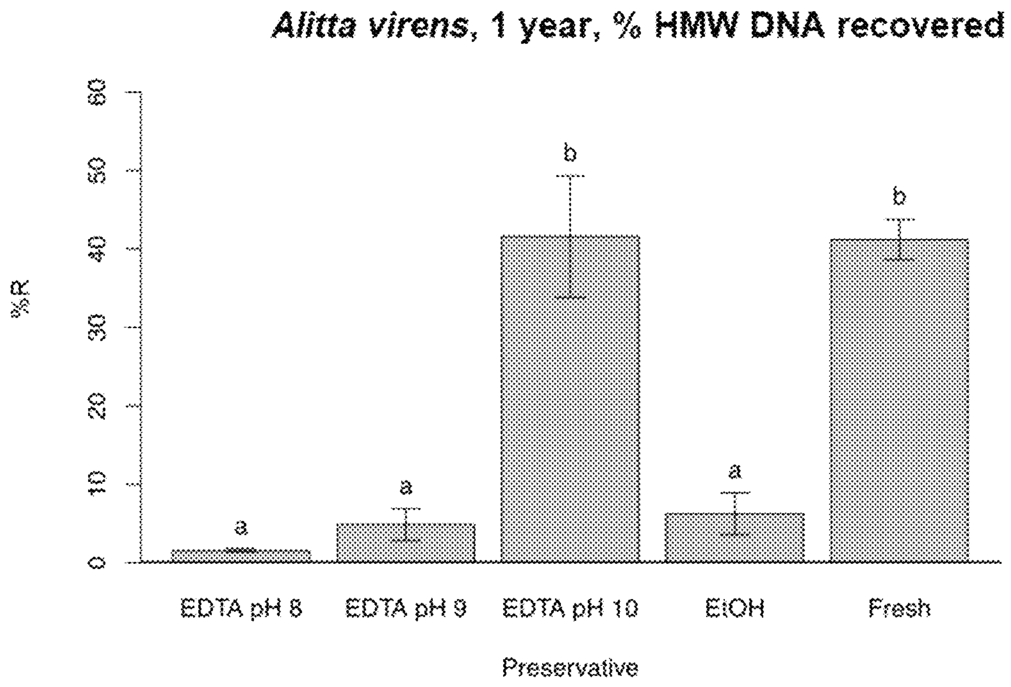
FIG. 11: Percent high molecular weight DNA recovered. Average percent high molecular weight DNA recovered (% R) was determined for tissues of *Alitta virens* extracted immediately from fresh tissue or stored for 1 year at room temperature in 0.25M EDTA, pH 8.0, 0.25M EDTA, pH 9.0, 0.25M EDTA, pH 10.0 and 95% ethanol. Error bars represent standard error. Within each histogram, treatments bearing different lower-case letters are significantly different at $p<0.05$, N=9; matching lower-case letters indicate statistically indistinguishable treatments. EtOH, 95% ethanol; Fresh, untreated tissue extracted immediately after dissection.
Figure 12:
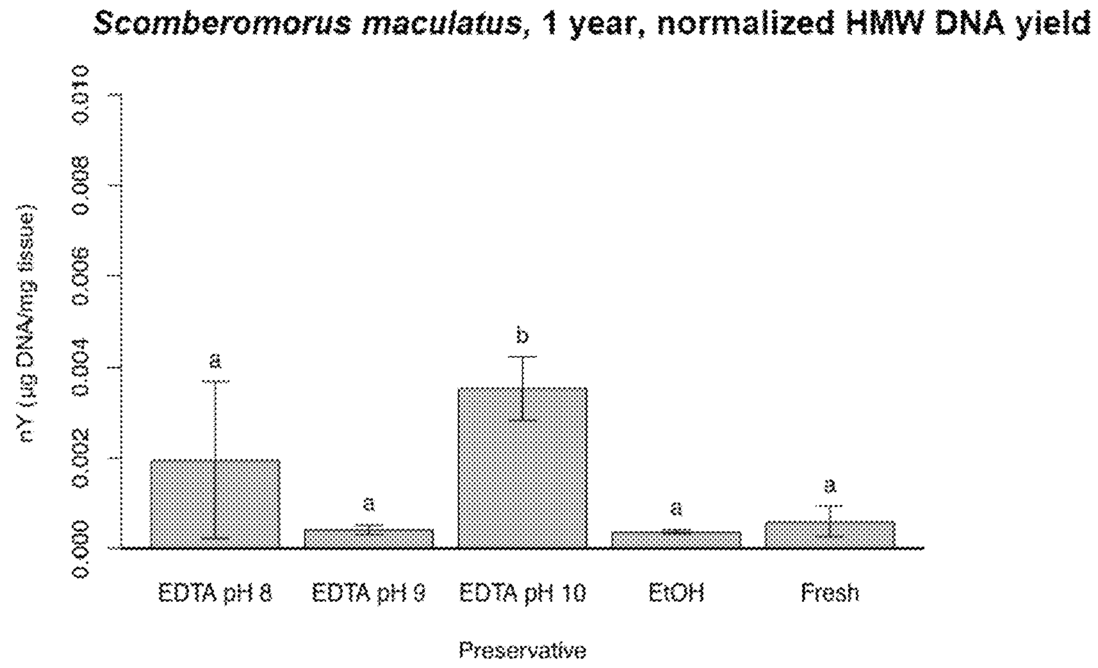
FIG. 12: Normalized high molecular weight DNA yield. Average normalized high molecular weight DNA yield (nY; μg DNA/mg tissue) was determined for tissues of *Scomberomorus maculatus* extracted immediately from fresh tissue or stored for 1 year at room temperature in 0.25 M EDTA, pH 8.0, 0.25 M EDTA, pH 9.0, 0.25 M EDTA, pH 10.0 and 95% ethanol. Error bars represent standard error. Treatments bearing different lower-case letters are significantly different at $p<0.05$, N=7; matching lower-case letters indicate statistically indistinguishable treatments. EtOH, 95% ethanol; Fresh, untreated tissue extracted immediately after dissection.
Figure 13:
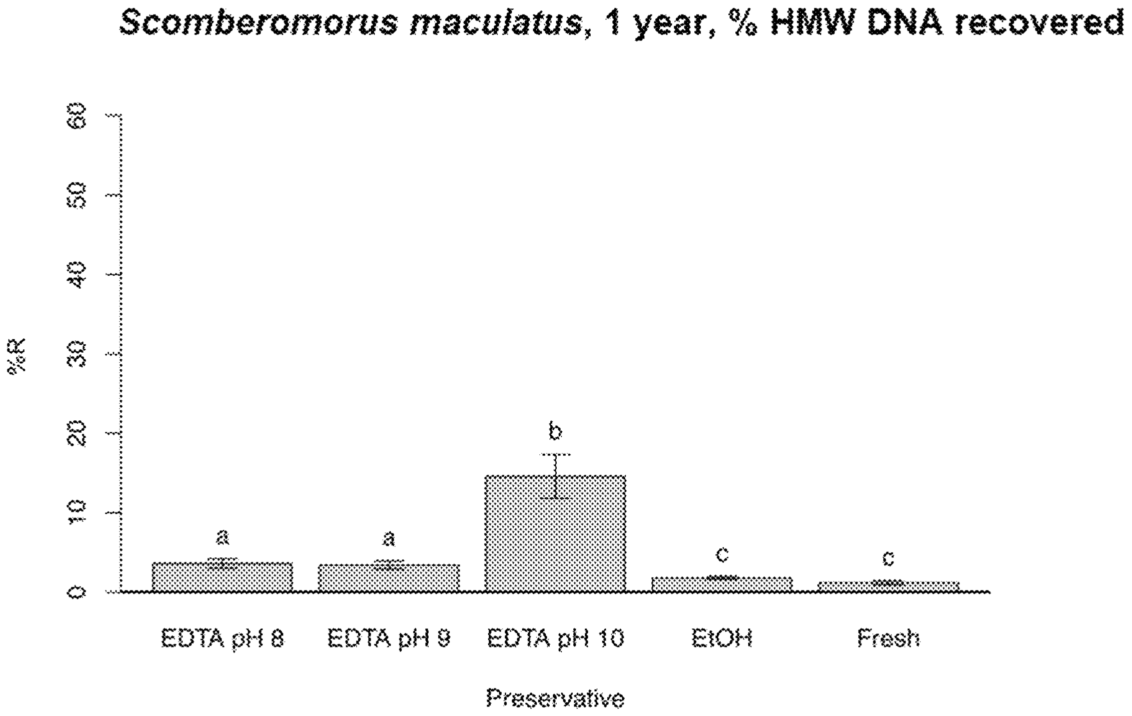
FIG. 13: Percent high molecular weight DNA recovered. Average percent high molecular weight DNA recovered (% R) was determined for tissues of *Scomberomorus maculatus* extracted immediately from fresh tissue or stored for 1 year at room temperature in 0.25 M EDTA, pH 8.0, 0.25 M EDTA, pH 9.0, 0.25 M EDTA, pH 10.0 and 95% ethanol. Error bars represent standard error. Treatments bearing different lower-case letters are significantly different at $p<0.05$, N=7; matching lower-case letters indicate statistically indistinguishable treatments. EtOH, 95% ethanol; Fresh, untreated tissue extracted immediately after dissection.

To test the ability of EDTA to slow degradation of high molecular weight DNA in tissue at increasing pH, EDTA solutions at pH 8.0, 9.0 and 10.0 were prepared. The tissues of 5 species of aquatic animals were stored in the resulting solutions at room temperature for periods ranging from 6 weeks to 12 months. As predicted, a substantial improvement in percent recovery of high molecular weight DNA was observed at higher pH values. This difference was primarily observed in tissue types that display a high rate of DNA degradation in other preservatives such as ethanol (EtOH) or DESS. Tissues of *A. virens* yielded little or no high molecular weight DNA after one year of storage in 95% ETOH, DESS or the tested variants of DESS at pH 8.0. However, preservation in EDTA at pH 10.0 resulted in values for normalized yield (FIG. 10) and percent recovery of high molecular weight DNA (FIG. 11) that are statistically indistinguishable from those observed for fresh tissue and that are significantly greater than those observed for EDTA at pH 8.0 or 95% ETOH. Also, preservation of tissues of *Scomberomorus maculatus* in EDTA at pH 10.0 resulted in values for normalized yield (FIG. 12) and percent recovery of high molecular weight DNA (FIG. 13) that are significantly greater than those observed for EDTA at pH 8.0 or 95% ETOH.

The observed differences in rates of DNA degradation may be attributed to differences in the DNase molecules found in these tissues. Those that either have a greater affinity for $Mg^{2+}$ or that are able to function at very low concentrations of $Mg^{2+}$ are able to degrade DNA in the presence of EDTA at pH 8.0. However, at pH 10, the concentration of the tetra-anionic form of EDTA is increased by orders of magnitude, thereby outcompeting these more aggressive DNases for binding $Mg^{2+}$.

Discussion

The ingredients of DESS, individually and in combination, were examined to determine the extent to which each contributes to the preservation of DNA in the tissues of three common aquatic organisms, *Mytilus edulis* (blue mussel), *Faxonius virilis* (virile crayfish) and *Alitta virens* (clam worm), under typical field and laboratory conditions.

The quality of DNA obtained from preserved biological specimens can be evaluated in many ways. Here, high molecular weight DNA was chosen as a proxy for DNA quality. While it is recognized that no single criterion can measure the suitability of a DNA sample for all applications, molecular weight is a simple, useful and easily measurable criterion that provides a first approximation of DNA quality. This is because many forms of DNA damage, including single and double strand breaks, loss or modification of bases and oxidation or chemical modifications of bonds, can directly or indirectly lead to a reduction of average molecular weight (Dawson, M. N. et al. 1998; Yoder, M. et al. 2006; Bester, E. W. et al. 1963; Nisha, K. et al. 2011). Moreover, high molecular weight DNA is desirable or required for use in many research applications (Camacho-Sanchez, M. et al. 2013; Permenter, J. et al. 2015; Mulcahy, D. G. et al. 2016). Indeed, the 'percent above threshold' approach used here has been proposed as a standard metric for reporting DNA quality (Mulcahy, D. G. et al. 2016). Here, high molecular weight DNA is defined as DNA with fragment lengths greater than 10 kb. The threshold was selected because this value corresponds roughly with the largest fragment size easily resolvable on agarose gels under typical lab conditions, is comparable to average gene lengths in many higher organisms and is similar to threshold values found in the literature (Kilpatrick C. W. 2002; Permenter, J. et al. 2015; Mulcahy, D. G. et al. 2016).

Quantitative data was collected using an Agilent Technologies TapeStation 2200 DNA Analyzer and genomic DNA ScreenTapes, which can measure the quantity and size distribution of DNA fragments in a sample over a range from 200 to 60,000 bp in length. It is noted that by failing to account for the largest and smallest DNA fragments, this method may underestimate % R and nY values for the best-preserved samples and overestimate % R and nY values for the least well-preserved samples. Thus, values at both extremes are expected to be conservative with respect to the model, i.e. less likely to reveal differences among treatments.

Given the finite size of the specimens used, it was not possible to design a factorial experiment that allowed for comparison among all individuals, taxa, treatments and time intervals. Therefore, the statistical analyses were limited to comparing the contributions of each of the three components of DESS to preservation of high molecular weight DNA at a given time interval. This was done by comparing the performance of DESS to solutions containing one of the three components of DESS alone or two components in all pairwise combinations. A factorial design was chosen that allowed for statistical comparison of these treatments within a given taxon and time interval. As a result, DNA preservation was not statistically compared across multiple storage intervals or the effectiveness of individual storage solutions among taxa. This approach allows us to isolate the effect of each component of DESS independent of taxon or specimen specific effects. While it may be interesting to assess patterns across time and taxa, these additional comparisons would primarily reveal differences in the relative rates of DNA degradation for different taxa rather than giving greater insight into the mechanisms underlying high molecular weight DNA preservation.

In this investigation, several trends were observed in patterns of DNA preservation. Most importantly, DESS-variant solutions containing EDTA performed as well or better than the comparable solution without EDTA. Specifically, for any given taxon and time interval, DESS, DE and ESS yielded equal or significantly greater % R and nY than DSS, D and SS, respectively. Consistent with this observation, solutions without EDTA performed poorly. In fact, it was observed that less than 5.71% R for all tissues stored in DESS-variant solutions without EDTA (i.e. DSS, D and SS) for all taxa at all time intervals greater than 1 day (FIG. 5). This is consistent with a previous study showing that DNA extractions from ant tissue stored in 20% DMSO saturated with NaCl yielded low DNA concentration and poor success in PCR amplification (Moreau, C. S. et al. 2013).

By comparison, solutions containing DMSO did not perform better than solutions without DMSO. Specifically, for most taxa and time intervals, solutions containing DMSO did not yield significantly greater % R or nY than those without DMSO (DESS, DE and DSS vs. ESS, E and SS, respectively; FIGS. 5 and 6). The single exception is that DSS yielded a very small but statistically significant increase in % R as compared to SS for *M. edulis* after storage for 3 months. However, average % R values for both SS (0.75%) and DSS (3.17%) were extremely low as compared to the worst EDTA-containing treatment, DE (40.20%), EtOH (15.37%) or fresh tissue (33.79%) for *M. edulis* at 3 months. Moreover, DSS did not outperform SS with respect nY for this taxon and time interval (FIG. 8). Thus, in this investigation, DMSO provided no substantial protection of high molecular weight DNA, nor did it substantially enhance the performance of other components of DESS.

Similarly, saturated NaCl alone provided no significant protection for high molecular weight DNA at time intervals greater than one day. For all taxa, storage in SS resulted in low % R (≤3.53%) and nY (≤0.0004 μg DNA/mg tissue). For both *M. edulis* and *F. virilis*, these values were significantly lower than those for fresh tissues or tissues stored in EtOH or any solution containing EDTA. In addition, no significant differences in % R and nY were observed between tissues stored in solutions with or without saturated NaCl (DESS, DSS and ESS vs. DE, D and E, respectively; FIGS. 5A-5F and 6A-6F). Interestingly, although saturated NaCl alone showed no effect in preserving high molecular weight DNA, it did appear to provide a slight indirect benefit to the preservation of high molecular weight DNA in certain contexts, i.e., only for *A. virens* and only in the presence of EDTA. At three and six months of storage, the addition of saturated NaCl to storage solutions containing EDTA (i.e. DESS and ESS) slightly but significantly improved % R and nY when compared to tissue stored in solutions containing EDTA without saturated NaCl (i.e., DE and E; FIGS. 5H, 5I, 6H and 6I). However, when EDTA was not present, the addition of saturated NaCl to another DESS component never significantly improved the % R or nY for any of the tested taxa (i.e. DSS vs. D).

Interestingly, the preservation of high molecular weight DNA in tissues of *A. virens* was poor for all preservatives tested, suggesting differences in the characteristics of the DNAse activity found in its tissue. Most DNase enzymes require magnesium or other divalent cations as cofactors (Yang, W. 2011; Gueroult, M. et al. 2010) and therefore their activity can be inhibited by divalent cation chelators like EDTA (Oviedo, C. et al. 2003; Graham, D. E. et al. 1978). If the tissue of *A. virens* includes nucleases that are capable of functioning at lower magnesium ion concentrations than those of the other taxa, or if they have greater affinity for magnesium ions than does EDTA, the inhibitory effect of EDTA may be diminished. Consistent with this interpretation, the performance of tested preservative solutions for *A. virens* at one day showed a similar pattern to those observed for the other taxa at 3 and 6 months, suggesting that similar processes may be occurring in all three taxa, although at different rates. The indirect effect of saturated NaCl on preservation by EDTA is also consistent with the potential role of EDTA as a chelator. Salt concentration can alter both the degree of dissociation of EDTA and its ability to chelate divalent cations (Spencer, C. P. 1958), potentially changing its effectiveness as a preservative. These hypotheses are testable and will be the topic of future investigations.

An additional experiment was performed to evaluate the performance of DNA extracts from EDTA-preserved tissues in a common application, PCR amplification and Sanger sequencing. Here, we PCR amplified and sequenced the barcode region (Hebert, P. D. et al. 2003) of the COI gene from DNA extracted from fresh tissues and those preserved in DESS and EDTA for 6 months. Good quality sequence was obtained from all samples regardless of preservative treatment, with the exception of one fresh tissue sample of *M. edulis*. Although slightly different sequences among individual specimens were observed, as is expected due to intraspecific variation, all sequences from a given individual were identical regardless of the preservation method.

For all species and storage intervals longer than 24 hours, tissue stored in solutions containing DMSO or NaCl alone or in combination yielded significantly lower % R than fresh tissue. For *M. edulis* and *F. virilis* at all storage intervals, tissues stored in solutions containing EDTA, either alone or in combination with DMSO and/or NaCl, yielded % R significantly greater than or equal to that of fresh tissue. For *A. virens* tissue stored for intervals longer than 24 hours, all solutions yielded significantly lower % R than fresh tissue. In no case did the addition of DMSO to a solution containing EDTA and/or NaCl improve the % R. Thus, in this study, only EDTA contributed directly to preservation of high molecular weight DNA.

In conclusion, it was found that under conditions in which DESS provided effective preservation of high molecular weight DNA (i.e. resulted in ≥20% R), all solutions containing EDTA (DE, ESS and E) were as or more effective than DESS (FIGS. 5A-5G). This is true for *M. edulis* and *F. virilis* at all time intervals, as well as for *A. virens* at one day. Conversely, when DESS was less effective as a preservative (i.e. resulted in <20% R), none of the six DESS-variant storage solutions provided better protection of high molecular weight DNA than DESS, as seen in *A. virens* after both three and six months of tissue storage (FIGS. 5H and 5I). These results indicate that for the taxa, treatments and time intervals examined, EDTA is the sole effective preservative component of DESS. These results are surprising in that they indicate that the eponymous ingredients, DMSO and NaCl, may not contribute to the effectiveness of DESS. Also, EDTA is less expensive, easier and safer to make and use than DESS, is not flammable and may be shipped by air without restrictions.

EDTA is widely in use as an anticoagulant in blood storage, and the improved quality of DNA recovered from blood stored in EDTA over that recovered from an alternative anticoalgulant (heparin) has been noted (Permenter, J. et al. 2015). EDTA is not recognized as a preservative for high molecular DNA in biological tissues.

REFERENCES CITED

Allen-Hall A, McNevin D. Human tissue preservation for disaster victim identification (DVI) in tropical climates. Forensic Science International: Genetics. 2012; 6 (5): 653-7.

Accession ID OGL-S29192-S29215 and S29350-S29455. The Ocean Genome Legacy Center. Northeastern University.

Beknazarova M, Millsteed S, Robertson G, Whiley H, Ross K. Validation of DESS as a DNA preservation method for the detection of *Strongyloides* spp. in canine feces. Int J Environ Res Public Health. 2017; 14 (6): 624.

Brayton C F. Dimethyl sulfoxide (DMSO): a review. The Cornell Veterinarian. 1986; 76 (1): 61-90.

Camacho-Sanchez M, Burraco P, Gomez-Mestre I, Leonard J A. Preservation of RNA and DNA from mammal samples under field conditions. Mol Ecol Resour. 2013; 13 (4): 663-73.

Corthals A, Martin A, Warsi O M, Woller-Skar M, Lancaster W, Russell A, et al. From the field to the lab: best practices for field preservation of bat specimens for molecular analyses. PLOS One. 2015; 10 (3): e0118994.

Dawson M N, Raskoff K A, Jacobs D K. Field preservation of marine invertebrate tissue for DNA analyses. Mol Marine Biol Biotechnol. 1998; 7 (2): 145-52. Epub 2001 Sep. 7.

Dessauer H C, Cole C J, Hafner M S. Collection and storage of tissues. In: Hillis D M, Moritz C, Mable B K, editors. Molecular Systematics. 2nd ed. Sunderland, MA: Sinauer Associates; 1996. p. 29-47.

Foottit R, Maw H, Havill N, Ahern R, Montgomery M. DNA barcodes to identify species and explore diversity in the Adelgidae (Insecta: Hemiptera: Aphidoidea). Mol Ecol Resour. 2009; 9:188-95.

Frantzen M, Silk J, Ferguson J, Wayne R, Kohn M. Empirical evaluation of preservation methods for faecal DNA. Mol Ecol. 1998; 7 (10): 1423-8.

Gaither M, Szabo' Z, Crepeau M, Bird C, Toonen R. Preservation of corals in salt-saturated DMSO buffer is superior to ethanol for PCR experiments. Coral Reefs. 2011; 30 (2): 329-33.

Graham D E. The isolation of high molecular weight DNA from whole organisms or large tissue masses. Anal Biochem. 1978; 85 (2): 609-13.

Gray M A, Pratte Z A, Kellogg C A. Comparison of DNA preservation methods for environmental bacterial community samples. FEMS Microbiol Ecol. 2013; 83 (2): 468-77.

Gueroult M, Picot D, Abi-Ghanem J, Hartmann B, Baaden M. How cations can assist DNase I in DNA binding and hydrolysis. PLOS Computational Biology. 2010; 6 (11): e1001000.

Hebert P D, Ratnasingham S, De Waard J R. Barcoding animal life: cytochrome c oxidase subunit 1 divergences among closely related species. Proc R Soc Lond B Biol Sci. 2003; 270 (Suppl 1): S96-S9.

Hernandez-Agreda A, Leggat W, Ainsworth T D. A comparative analysis of microbial DNA preparation methods for use with massive and branching coral growth forms. Front Microbiol. 2018; 9:2146.

Kilpatrick C W. Noncryogenic preservation of mammalian tissues for DNA extraction: an assessment of storage methods. Biochem Genet. 2002; 40 (1-2): 53-62.

Michaud C L, Foran D R. Simplified field preservation of tissues for subsequent DNA analyses. J Forensic Sci. 2011; 56 (4): 846-52.

Moreau C S, Wray B D, Czekanski-Moir J E, Rubin B E. DNA preservation: a test of commonly used preservatives for insects. Invertebr Syst. 2013; 27 (1): 81-6.

Mulcahy D G, Macdonald K S III, Brady S G, Meyer C, Barker K B, Coddington J. Greater than X kb: a quantitative assessment of preservation conditions on genomic DNA quality, and a proposed standard for genome-quality DNA. PeerJ. 2016; 4: e2528.

Nagy Z T. A hands-on overview of tissue preservation methods for molecular genetic analyses. Org Divers Evol. 2010; 10 (1): 91-105.

Nester E W, Ganesan A, Lederberg J. Effects of mechanical shear on genetic activity of *Bacillus subtilis* DNA. Proc Natl Acad Sci USA. 1963; 49 (1): 61.

Nisha K, Deshwal R. Antioxidants and their protective action against DNA damage. DNA. 2011; 27 (28): 28-32.

Oviedo C, Rodri guez J. EDTA: the chelating agent under environmental scrutiny. Quim Nova. 2003; 26 (6): 901-5.

Permenter J, Ishwar A, Rounsavall A, Smith M, Faske J, Sailey C J, et al. Quantitative analysis of genomic DNA degradation in whole blood under various storage conditions for molecular diagnostic testing. Mol Cell Probe. 2015; 29 (6): 449-53.

Proebstel S. Preservation of nonfrozen tissue samples from a salmonine fish Brachymystax lenok (Pallas) for DNA analysis. J Ichthyol. 1993; 32:9-17.

Robertson K M, Minich J, Bowman A J, Morin P A. A thin soup: extraction and amplification of DNA from DMSO and ethanol used as preservative for cetacean tissue samples. Conserv Genet Resour. 2013; 5 (4): 929-33.

Rocha J, Coelho F J, Peixe L, Gomes N C, Calado R. Optimization of preservation and processing of sea anemones for microbial community analysis using molecular tools. Sci Rep. 2014; 4:6986.

Santini A, Lucchini V, Fabbri E, Randi E. Ageing and environmental factors affect PCR success in wolf (*Canis lupus*) excremental DNA samples. Mol Ecol Notes. 2007; 7 (6): 955-61.

Seutin G, White B N, Boag P T. Preservation of avian blood and tissue samples for DNA analyses. Can J Zool. 1991; 69 (1): 82-90.

Sharpe, A., S. Barrios, S. Gayer, E. Allan-Perkins, D. Stein, H. J. Appiah-Madson, R. Falco and D. L. Distel. DESS deconstructed: Is EDTA solely responsible for protection of high molecular weight DNA in this common tissue preservative?" PLOS ONE. 2020; 15 (8): e0237356.

Spencer C P. The chemistry of ethylenediamine tetra-acetic acid in sea water. J Mar Biolog Assoc UK. 1958; 37 (1): 127-44.

Vink C J, Thomas S M, Paquin P, Hayashi C Y, Hedin M. The effects of preservatives and temperatures on arachnid DNA. Invertebr Syst. 2005; 19 (2): 99-104.

Williams S. Safe and legal shipment of tissue samples: does it affect DNA quality? J Molluscan Stud. 2007; 73 (4): 416-8.

Yang W. Nucleases: diversity of structure, function and mechanism. Q Rev Biophys. 2011; 44 (1): 1.

Yoder M, King I W, De Ley I T, Mann J, Mundo-Ocampo M, Poiras L, et al. DESS: a versatile solution for preserving morphology and extractable DNA of nematodes. Nematology. 2006; 8 (3): 367-76.

INCORPORATION BY REFERENCE

All of the U.S. patents and U.S. and PCT published patent applications cited herein are hereby incorporated by reference.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A method for preserving high molecular weight DNA in a biological tissue, consisting of contacting for a period of time at a temperature the biological tissue with an aqueous solution consisting of water and a compound having the structure:

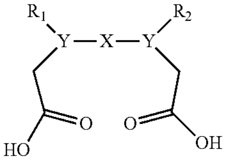

wherein

X is alkyl, alkyl-$X_1$-alkyl, alkyl-$X_1$-alkyl-$X_1$-alkyl, aryl-$X_1$-alkyl-$X_1$-aryl, or $X_2$-alkyl-$X_2$, provided that when X is $X_2$-alkyl-$X_2$, then each Y is CH;

$X_1$, for each occurrence, is independently O, C(H)($R_3$), or $NR_4$;

$X_2$, for each occurrence, is N;

Y, for each occurrence, is independently CH or N;

$R_1$ is —$CO_2H$, -alkyl-OH, or -alkyl-$CO_2H$, provided that when X is $X_2$-alkyl-$X_2$, then when $R_1$ is —$CO_2H$, then the adjacent Y is CH;

$R_2$ is —$CO_2H$, -alkyl-OH, or -alkyl-$CO_2H$, provided that when X is $X_2$-alkyl-$X_2$, then when $R_2$ is —$CO_2H$, then the adjacent Y is CH;

$R_3$ is —OH, —$CO_2H$, or -alkyl-$CO_2H$; and $R_4$ is -alkyl-$CO_2H$, thereby preserving the high molecular weight DNA in the biological tissue, wherein the pH of the aqueous solution is about 10.

2. The method of claim 1, wherein the biological tissue is a mammalian tissue, an arthropod tissue, an amphibian tissue, a bivalve tissue, or a fish tissue.

3. The method of claim 1, wherein the concentration of the compound in the aqueous solution is about 0.1-1 M.

4. The method of claim 1, wherein the period of time is 1 day to 6 months.

5. The method of claim 1, wherein the temperature is room temperature.

6. The method of claim 1, wherein the compound has the structure:

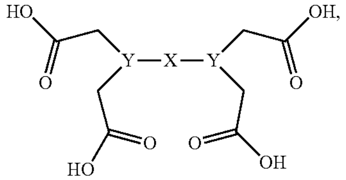

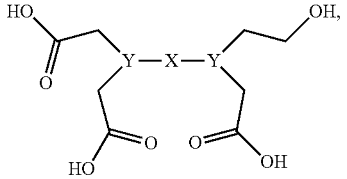

or

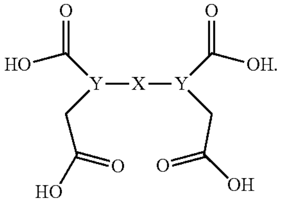

7. The method of claim 6, wherein each Y is N.

8. The method of claim 1, wherein $R_1$ and $R_2$ are each —$CH_2CO_2H$; or $R_1$ and $R_2$ are each —$CO_2H$, or $R_1$ is $CH_2OH$ and $R_2$ is —$CH_2CO_2H$.

9. The method of claim 1, wherein the compound has the structure:

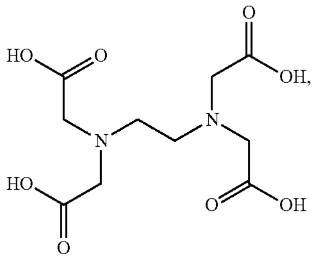

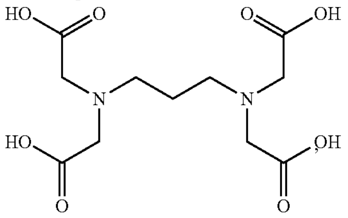

-continued
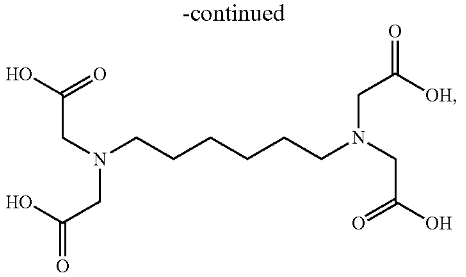
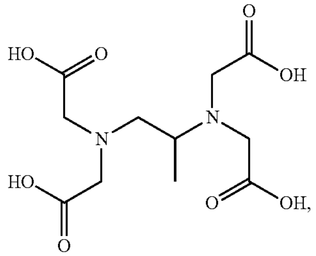
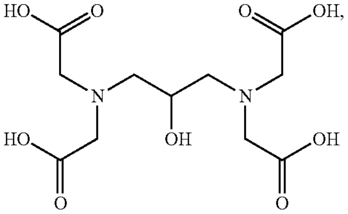
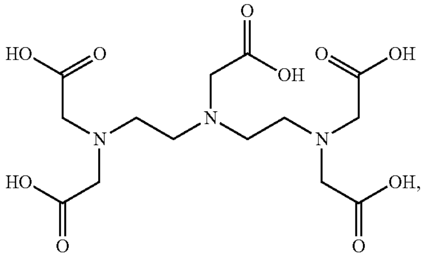
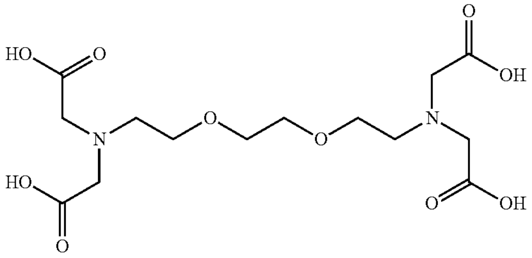
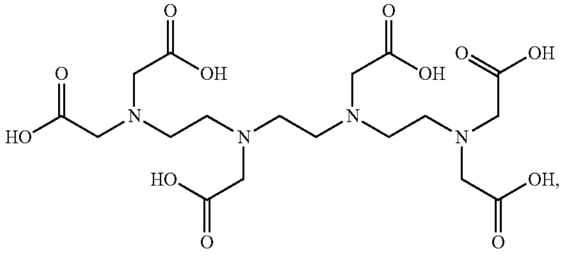
-continued
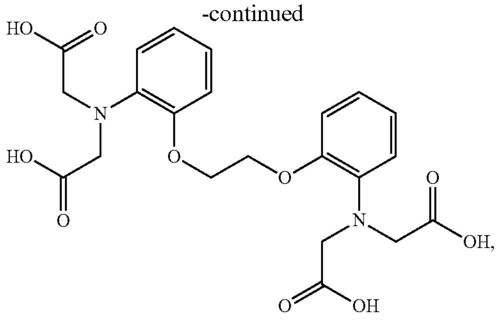
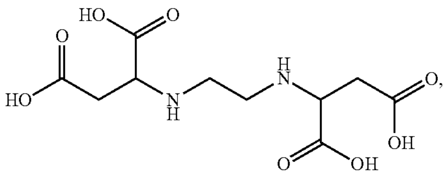
or
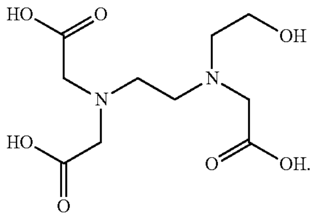
10. The method of claim 1, wherein the compound has the structure:
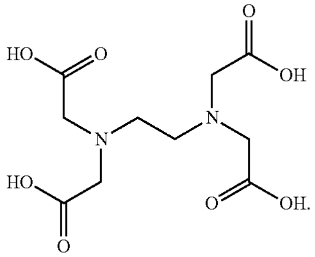 [SMILES: O=C(O)CN(CCN(CC(=O)O)CC(=O)O)CC(=O)O]
11. The method of claim 1, wherein the concentration of the compound in the aqueous solution is about 0.25 M.
12. The method of claim 1, wherein the concentration of the compound in the aqueous solution is about 0.5 M.
* * * * *